US010512763B2

(12) United States Patent
Jenkins et al.

(10) Patent No.: US 10,512,763 B2
(45) Date of Patent: Dec. 24, 2019

(54) DILATION CATHETER WITH EXPANDABLE STOP ELEMENT

(71) Applicant: Acclarent, Inc., Menlo Park, CA (US)

(72) Inventors: Thomas R. Jenkins, Alameda, CA (US); Randy J. Kesten, Mountain View, CA (US)

(73) Assignee: Acclarent, Inc., Irvine, CA (US)

( * ) Notice: Subject to any disclaimer, the term of this patent is extended or adjusted under 35 U.S.C. 154(b) by 346 days.

(21) Appl. No.: 14/834,968

(22) Filed: Aug. 25, 2015

(65) Prior Publication Data

US 2017/0056632 A1      Mar. 2, 2017

(51) Int. Cl.
| | |
|---|---|
| *A61M 29/02* | (2006.01) |
| *A61B 17/24* | (2006.01) |
| *A61M 25/00* | (2006.01) |
| *A61M 25/01* | (2006.01) |
| *A61M 25/10* | (2013.01) |

(52) U.S. Cl.
CPC .............. *A61M 29/02* (2013.01); *A61B 17/24* (2013.01); *A61M 25/0074* (2013.01); *A61M 25/0113* (2013.01); *A61M 25/1011* (2013.01); *A61M 2025/1093* (2013.01); *A61M 2029/025* (2013.01)

(58) Field of Classification Search
CPC .............. A61M 29/02; A61M 25/0074; A61M 25/1011; A61M 2025/1013; A61M 2025/1015; A61M 2029/025; A61M 25/1018; A61M 25/10181; A61B 2017/242; A61B 2017/246; A61B 2017/248; A61B 17/12104; A61B 17/24
See application file for complete search history.

(56) References Cited

U.S. PATENT DOCUMENTS 6,669,711 B1 * 12/2003 Noda ............... A61B 17/12104
                                                                      604/907
6,716,813 B2    4/2004 Lim et al.
(Continued)

FOREIGN PATENT DOCUMENTS

WO     WO 2011/140535 A1    11/2011

OTHER PUBLICATIONS

International Search Report and Written Opinion dated Oct. 26, 2016 for Application No. PCT/US2016/042901, 15 pgs.

*Primary Examiner* — Todd J Scherbel
*Assistant Examiner* — Brooke Labranche
(74) *Attorney, Agent, or Firm* — Frost Brown Todd LLC

(57) ABSTRACT

A catheter system includes a balloon dilation catheter. The balloon dilation catheter includes an elongate shaft, an expandable dilation balloon, and an expandable stop element. The elongate shaft has a dilation balloon lumen that is configured to couple with a first fluid supply. The expandable dilation balloon is coupled to the elongate shaft and is fluidly connected to the dilation balloon lumen. The expandable dilation balloon is configured to transition between an inflated state and a non-inflated state. The expandable stop element is distal to the expandable dilation balloon. The expandable stop element is configured to transition between an expanded state and a non-expanded state. The expanded dilation balloon is configured to define a larger outer diameter in the inflated state than an outer diameter defined by the expandable stop element in the expanded state.

9 Claims, 15 Drawing Sheets

(56) References Cited

U.S. PATENT DOCUMENTS

| | | |
|---|---|---|
| 7,645,272 B2 | 1/2010 | Chang et al. |
| 7,645,296 B2 | 1/2010 | Theron et al. |
| 7,654,997 B2 | 2/2010 | Makower et al. |
| 7,803,150 B2 | 9/2010 | Chang et al. |
| 8,834,513 B2 | 9/2014 | Hanson et al. |
| 8,894,614 B2 | 11/2014 | Muni et al. |
| 9,155,492 B2 | 10/2015 | Jenkins et al. |
| 9,554,817 B2 | 1/2017 | Goldfarb et al. |
| 2006/0004323 A1 | 1/2006 | Chang et al. |
| 2010/0030031 A1 | 2/2010 | Goldfarb et al. |
| 2010/0274188 A1 | 10/2010 | Chang et al. |
| 2011/0004057 A1 | 1/2011 | Goldfarb et al. |
| 2012/0071727 A1* | 3/2012 | Hanson .................. A61B 17/24 600/249 |
| 2014/0276135 A1* | 9/2014 | Agah .................... A61M 5/142 600/485 |
| 2015/0150436 A1* | 6/2015 | Cornhill ............. A61B 1/00082 600/104 |
| 2015/0164571 A1* | 6/2015 | Saadat .................. A61B 17/24 600/109 |
| 2015/0258315 A1* | 9/2015 | Chandler ........ A61M 25/10182 600/249 |
| 2015/0374963 A1 | 12/2015 | Chan et al. |
| 2016/0317791 A1* | 11/2016 | Gross ................. A61M 25/1011 |

\* cited by examiner

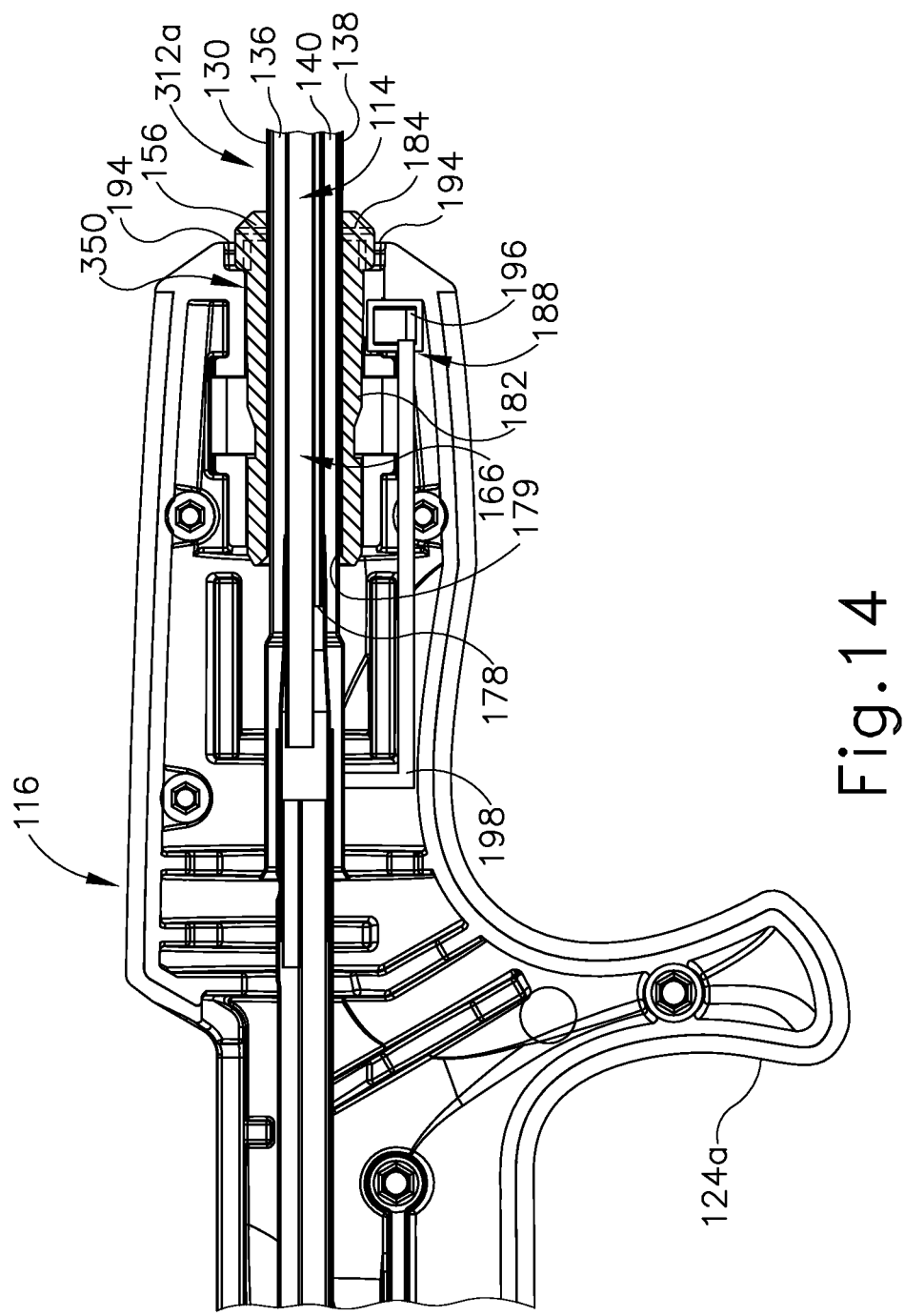

DILATION CATHETER WITH EXPANDABLE STOP ELEMENT

BACKGROUND

In some instances, it may be desirable to dilate an anatomical passageway in a patient. This may include dilation of the Eustachian tube, dilation of ostia of paranasal sinuses (e.g., to treat sinusitis), dilation of the larynx, or dilation of other passageways within the ear, nose, or throat, etc. One method of dilating anatomical passageways includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pat. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Reneva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, issued as U.S. Pat. No. 9,155,492 on Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

It may be desirable to provide easily controlled dilation of various kinds of anatomical passageways in a patient using a single instrument, including procedures that will be performed only by a single operator. While several systems and methods have been made and used to dilate anatomical passageways in a patient, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 14 depicts an enlarged cross-sectional view of an intermediate portion of the dilation catheter system of FIG. 7, with one of the guide catheters of FIG. 13 fully assembled with the remainder of the dilation catheter system.

Figure 1:
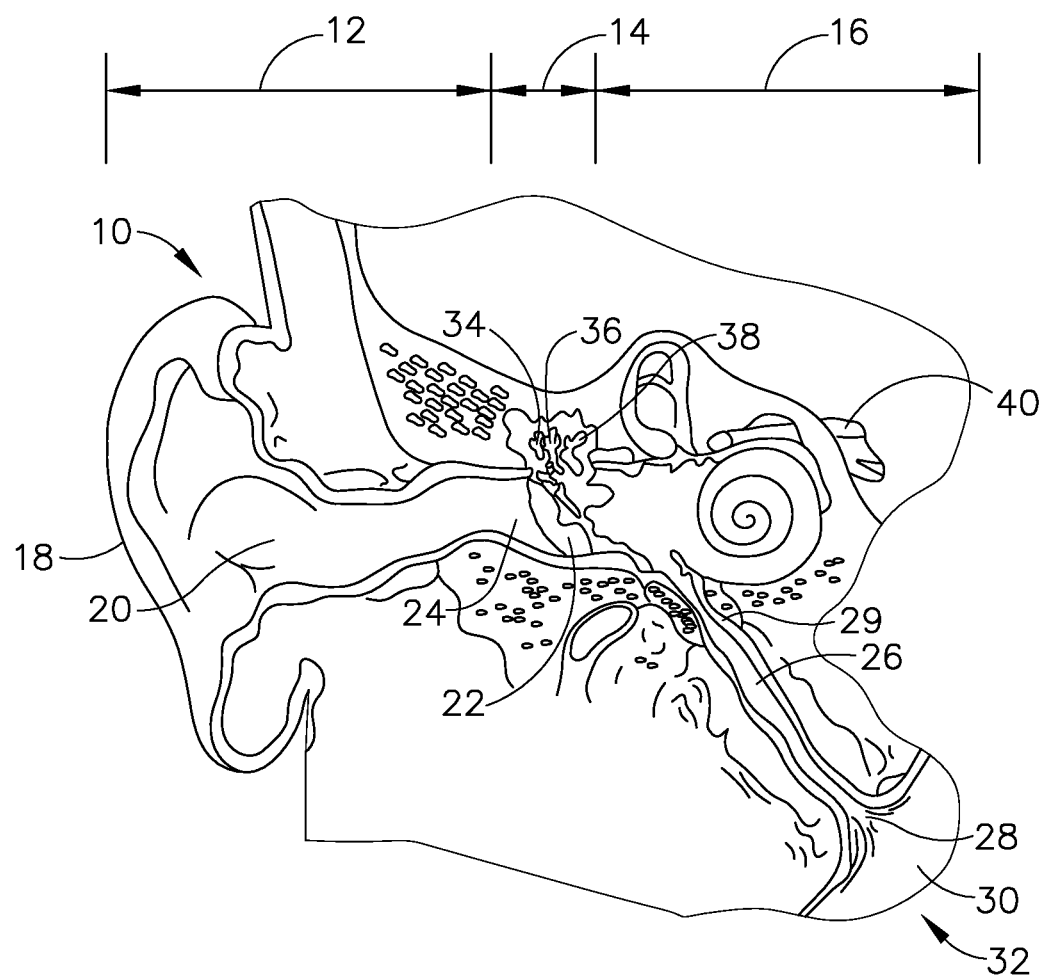
FIG. 1 depicts a cross-sectional front view of a human ear showing the inner, middle, and outer ear portions and the Eustachian tube connecting the middle ear with the nasopharynx region of the throat via a pharyngeal ostium thereof.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Methods of Treating the Middle Ear and Eustachian Tube

Figure 2:
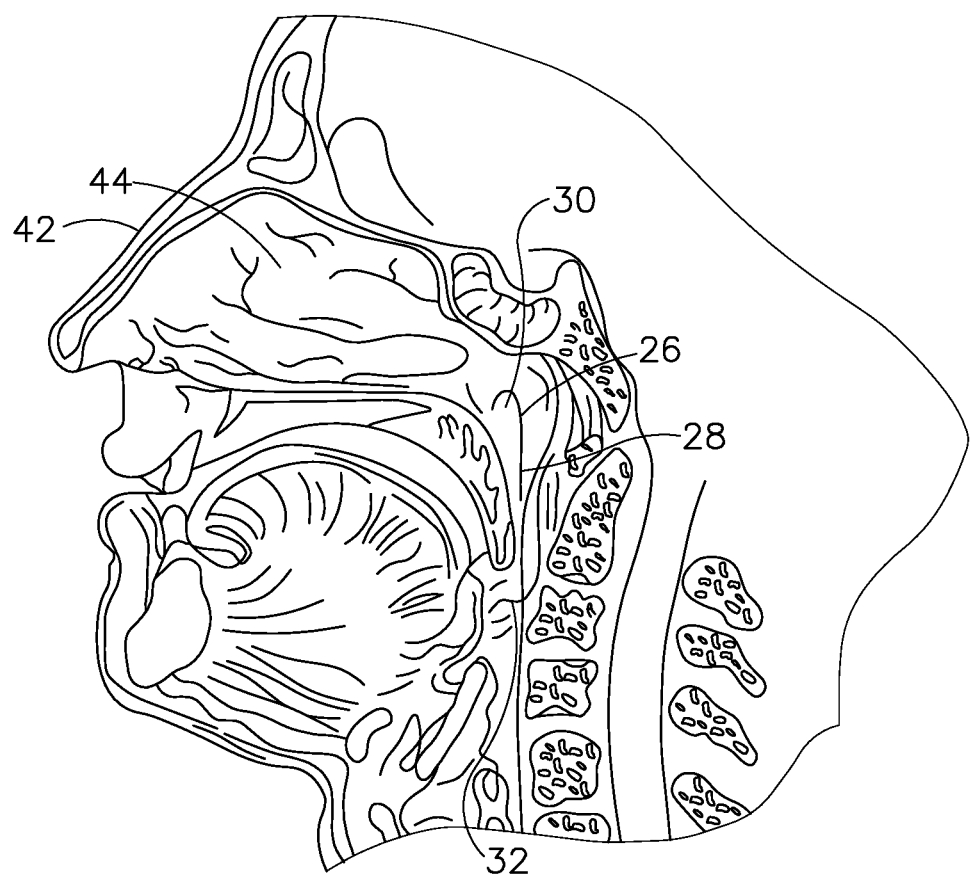
FIG. 2 depicts a cross-sectional side view of a human head showing the nasopharynx region of the throat illustrated in FIG. 1 containing the pharyngeal ostium of the Eustachian tube illustrated in FIG. 1.

FIGS. 1 and 2 show an ear (10) comprising three parts: an external ear (12), a middle ear (14) and an inner ear (16). External ear (12) includes an auricle (18) and an ear canal (20) that gather sound and direct it towards a tympanic membrane (22) (also referred to as the eardrum) located at an inner end (24) of the ear canal (20). Middle ear (14) lies between the external and inner ears (12) and (16) and is connected to the back of the throat by a Eustachian tube (26) which serves as a pressure equalizing valve between ear (10) and the sinuses. Eustachian tube (26) terminates in an opening or ostium (28) in the nasopharynx region (30) of the throat (32). In addition to tympanic membrane (22), middle ear (14) also includes three small ear bones (ossicles): a malleus (34) (hammer), an incus (36) (anvil) and a stapes (38) (stirrup). These bones (34, 36, 38) transmit sound vibrations to inner ear (16) and thereby act as a transformer, converting sound vibrations in canal (20) of external ear (12) into fluid waves in inner ear (16). These fluid waves stimulate several nerve endings (40) that, in turn, transmit sound energy to the brain where it is interpreted.

Eustachian tube (26) is shown as a narrow, two to two-and-a-half centimeter long channel, measured from ostium (28) to isthmus (29), connecting middle ear (14) with nasopharynx (30). Eustachian tube (26) functions as a pressure equalizing valve for middle ear (14), which is normally filled with air. Typically, Eustachian tube (26) opens for a fraction of a second periodically in response to swallowing or yawning. In so doing, it allows air into middle ear (14) to replace air that has been absorbed by the middle ear lining (mucous membrane) or to equalize pressure changes occurring on altitude changes. Anything that interferes with this periodic opening and closing of Eustachian tube (26) may result in hearing impairment or other ear symptoms.

Obstruction or blockage of Eustachian tube (26) results in a negative middle ear pressure (14), with retraction (sucking in) of tympanic membrane (22). In adults, this may be accompanied by some ear discomfort, a fullness or pressure feeling, and may result in a mild hearing impairment and/or head noise (tinnitus). There may be no symptoms in children. If the obstruction is prolonged, fluid may be drawn from the mucous membrane of middle ear (14), creating a condition referred to as serous otitis media (fluid in the middle ear). This may occur in children in connection with an upper respiratory infection and may account for hearing impairment associated with this condition.

A lining membrane (mucous membrane) of middle ear (14) and Eustachian tube (26) is connected with, and is the same as, the membrane of nose (42), sinuses (not shown) and throat (32). Infection of these areas results in mucous membrane swelling, which in turn may result in obstruction of Eustachian tube (26). This may ultimately result in acute or chronic serous otitis media, with fluid accumulating in middle ear (14). In the presence of bacteria, this fluid may become infected, leading to what may be referred to as an acute suppurative otitis media (infected or abscessed middle ear). When infection does not develop, the fluid remains until Eustachian tube (26) again begins to function normally, at which time the fluid is absorbed or drains down the Eustachian tube (26) into throat (32) through Eustachian tube ostium (28).

Chronic serous otitis media may result from long standing Eustachian tube blockage, or from thickening of the fluid so that it cannot be absorbed or drained down Eustachian tube (26). Under some circumstances, this chronic condition may be associated with hearing impairment. There may also be recurrent ear pain. Fortunately, serous otitis media may persist for many years without producing any permanent damage to middle ear (14). The presence of fluid in middle ear (14), however, makes it very susceptible to recurrent acute infections. These recurrent infections may result in middle ear damage.

When Eustachian tube (26) contains a build-up of fluid, a number of things may occur. First, the body may absorb the air from middle ear (14), thus causing a vacuum to form. Such a vacuum may tend to pull the lining membrane and ear drum (22) inwardly, causing pain. Next, the body may replace the vacuum with more fluid, which may tend to relieve pain, but the patient may experience a fullness sensation in ear (10). Treatment of this condition with antihistamines and decongestants can take many weeks to be fully effective. Finally, the fluid may become infected, which may be painful and may lead to other conditions associated with such an infection such as fever and/or hearing loss or degradation. If inner ear (14) is affected by such an infection, the patient may experience dizziness or disorientation—symptoms typically associated with the condition of vertigo.

Although the above described symptoms may be treated with antihistamines, decongestants, and antibiotics, such pharmaceuticals may be less desirable because they may not produce immediate resolution of symptoms caused by buildup of fluid in middle ear (14). Thus, immediate relief may be achieved by simply removing the fluid from Eustachian tube (26). Moreover, while administration of the pharmaceuticals described above may eventually resolve the infection, such treatment may not resolve the underlying issue of improper functioning of Eustachian tube (26). Accordingly, it may be desirable to perform surgical treatments of chronic serous otitis media to both achieve immediate relief of symptoms and to resolve any underling issues with Eustachian tube (26) function.

Figure 3:
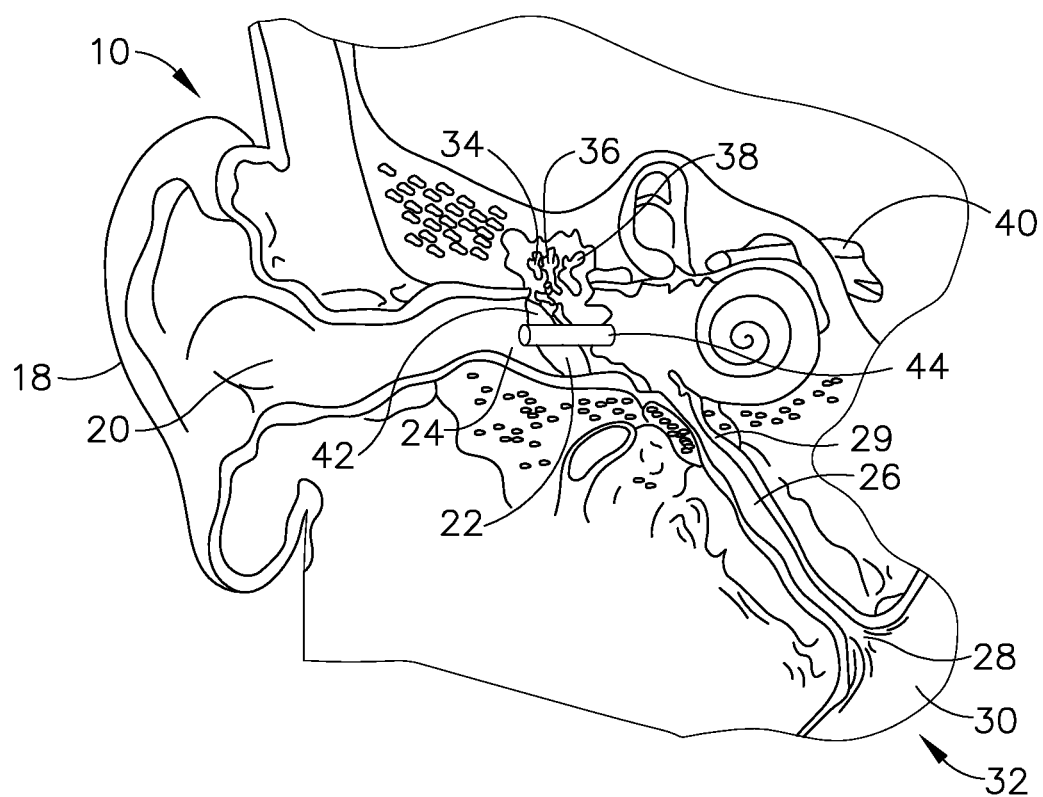
FIG. 3 depicts a cross-sectional front view of a human ear showing a surgical method for relieving fluid in the middle ear in which a ventilation tube is placed within an incision in the tympanic membrane.

FIG. 3 shows a myringotomy procedure, which may be performed to relieve fluid in middle ear (14). For instance, an incision (42) may be formed in tympanic membrane (22) to drain or remove fluid from middle ear (14). A hollow plastic tube (44) may be inserted and/or lodged in incision (42) to prevent incision (42) from self-sealing, thereby maintaining ventilation of middle ear (14) over an extended period of time. Thus during a treatment period, ventilation tube (44) temporarily takes the place of the Eustachian tube (26), performing the function of equalizing the pressure in middle ear (14). In some instances, the treatment period may last for a period of three to nine months. Such a period may permit the Eustachian tube (26) blockage to subside. After the treatment period, ventilation tube (44) may naturally dislodge and tympanic membrane (22) may self-seal. Alternatively, ventilation tube (44) may be removed surgically by a medical professional. Regardless of how ventilation tube (44) is removed, Eustachian tube (26) may resume its typical function after the treatment period.

Figure 4:
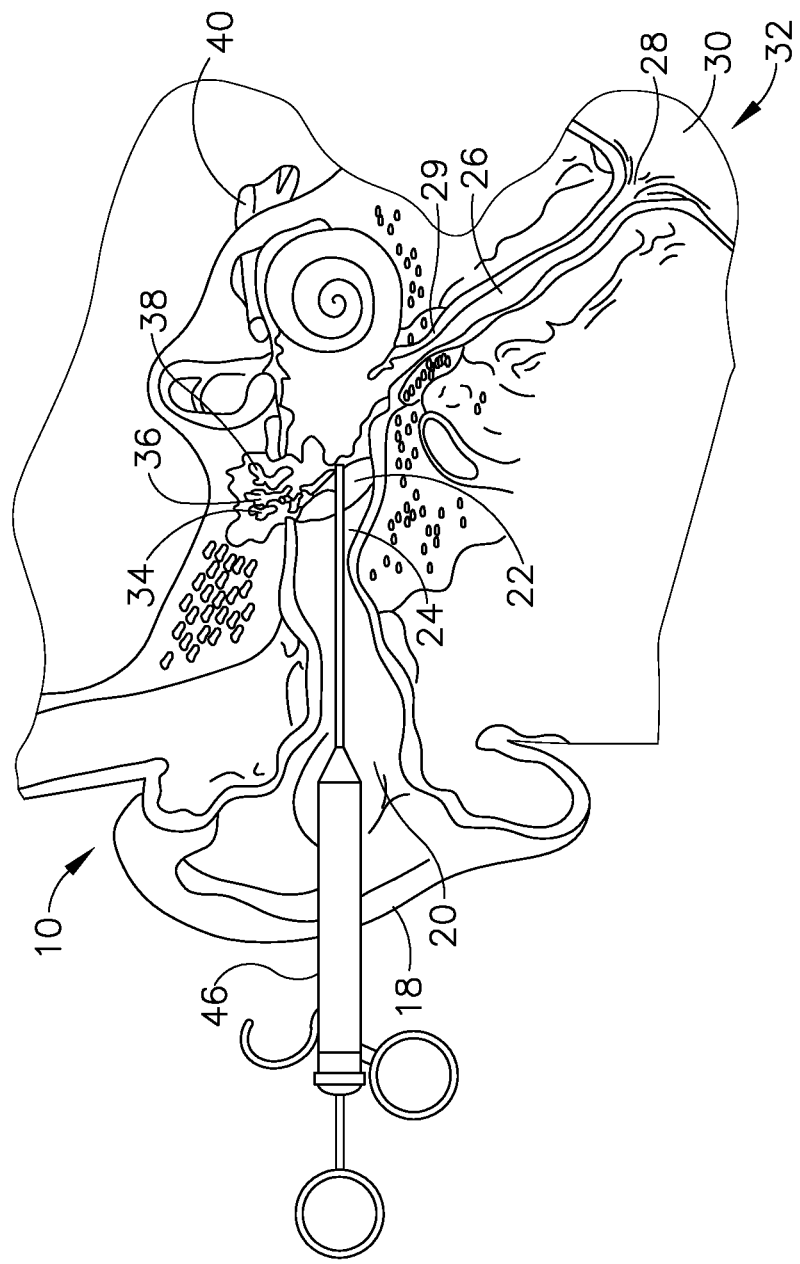
FIG. 4 depicts a cross-sectional front view of a human ear showing another surgical method for relieving fluid in the middle ear in which a syringe is shown having a needle perforating the tympanic membrane.

FIG. 4 shows an exemplary alternative method of relieving middle ear (14) pressure. As can be seen, a hypodermic needle (46) is driven through tympanic membrane (22). Hypodermic needle (46) may then be used to manually withdraw fluid from middle ear (14). However, it should be understood that such a procedure shown in FIG. 4 may only result in removal of fluid from the upper portion of Eustachian tube (26). Thus, while effective at removing fluid from middle ear (14), some fluid may still remain when the procedure shown in FIG. 4 is used.

Although the procedures shown in FIGS. 3 and 4 may be effective in treating fluid buildup in middle ear (14), such procedures may be undesirable because both procedures involve a creating a perforation in tympanic membrane (22). Procedures leading to a perforation of tympanic membrane (22) may be undesirable because, in some instances, such a perforation could become permanent. Moreover, although the procedures described above may remove fluid from middle ear (14), the underlying problem of a blocked Eustachian tube (26) may remain.

Figure 5:
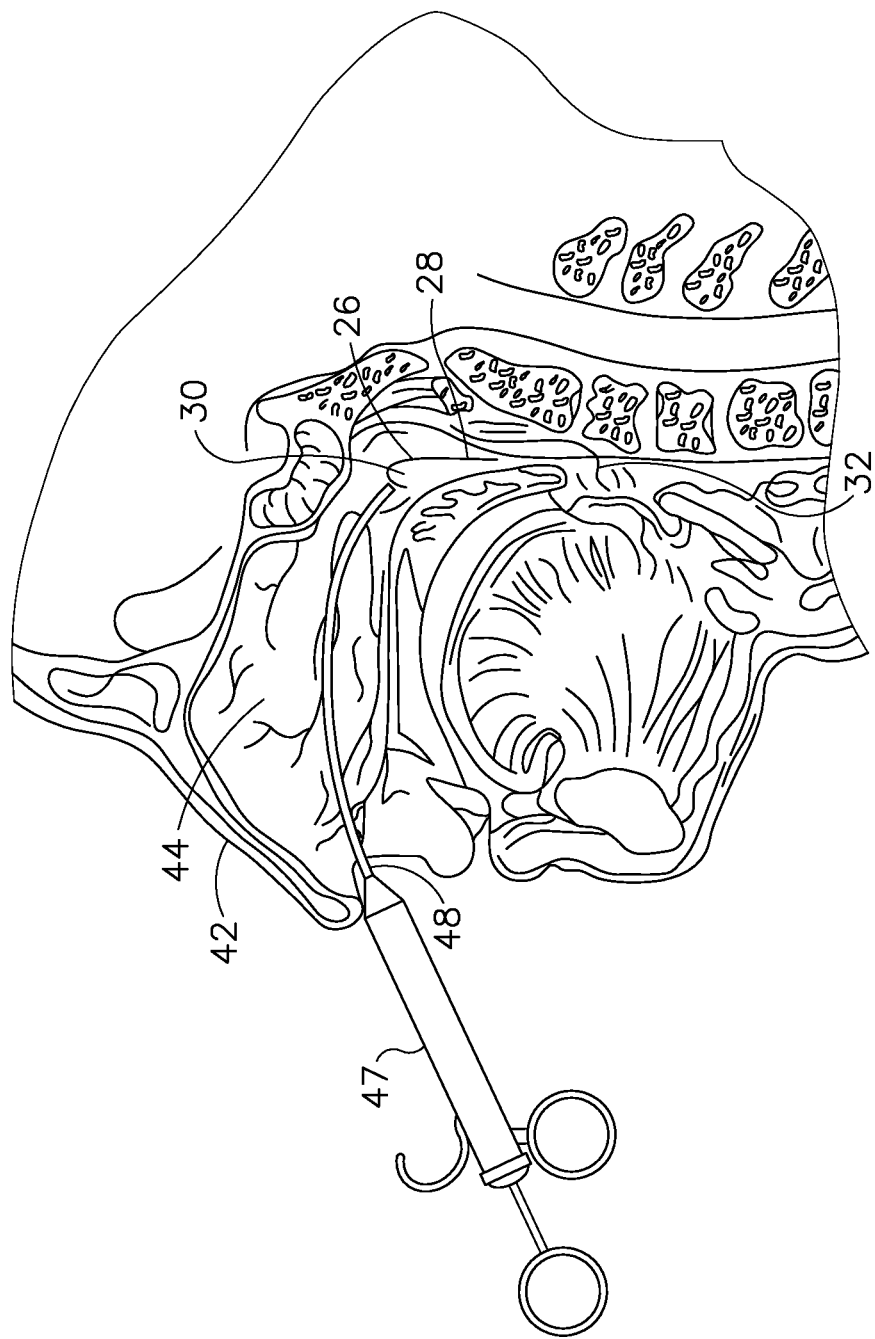
FIG. 5 depicts a cross-sectional side view of a human head showing a politzerization method for relieving fluid in the middle ear in which a syringe is shown having a flexible tip extending into the nose and/or throat area so that the tip abuts the pharyngeal ostium of the Eustachian tube while the nose is plugged.
Figure 6:
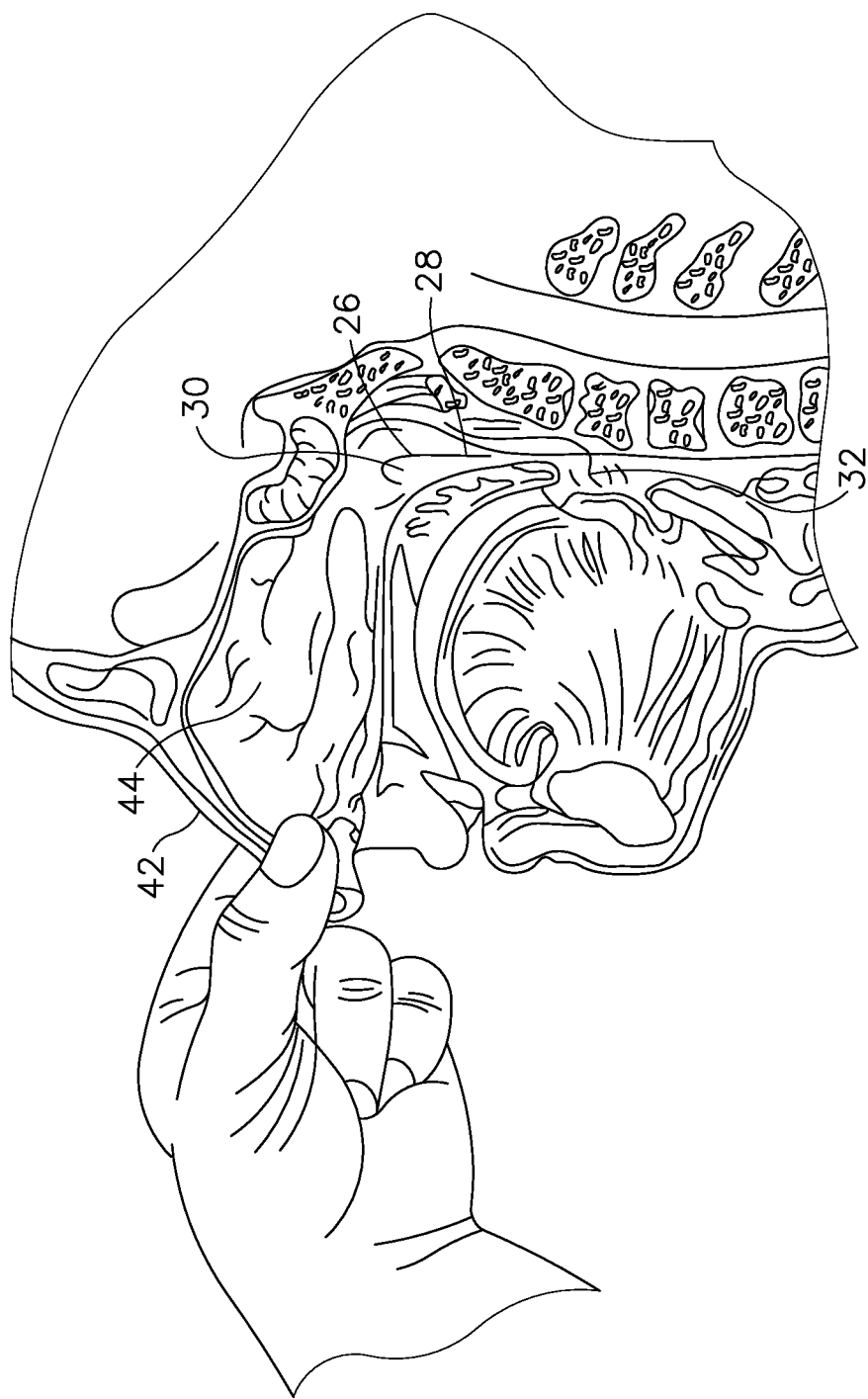
FIG. 6 depicts a cross-sectional side view of a human head showing the politzerization method of FIG. 5 while the nose is plugged.

Another exemplary alternative procedure for treating fluid buildup in middle ear (14) is shown in FIGS. 5 and 6. As can best be seen in FIG. 5, a hypodermic syringe (47) with a flexible tip (48) is shown as being inserted into a nostril to position flexible tip (48) adjacent to ostium (28) of Eustachian tube (26) within nasopharynx (30). Syringe (47) may then be used to inject air or fluid through flexible tip (48) and into Eustachian tube (26). The force of the air traveling into Eustachian tube (26) may relieve congestion and reestablish middle ear (14) ventilation. In some circumstances this procedure may be referred to as politzerization. As shown in FIG. 6, such a procedure may optionally be performed while the nostrils are pinched shut with the patient simultaneously swallowing. Such a technique may aid in forcing air into Eustachian tube (26). While the procedure described above may be effective at opening Eustachian tube (26), it should be understood that the procedure does not necessarily clear fluid away from middle ear (14).

While not shown, it should be understood that a similar procedure to the politzerization procedure described above may be performed. Such a procedure may be referred to as a "valsalva" maneuver and may be accomplished by the patient forcibly blowing air into middle ear (14) while holding the nostrils closed. Such a procedure may also be colloquially referred to as "popping" the ear. While this procedure may open Eustachian tube (26), it should be understood that it may not necessarily lead to fluid being cleared from middle ear (14). Further procedures for treatment of fluid buildup in middle ear (14) are described in U.S. patent application Ser. No. 14/317,269, entitled "Vent Cap for a Eustachian Tube Dilation System," filed Jun. 29, 2014, issued as U.S. Pat. No. 10,350,396 on Jul. 16, 2019; and U.S. Pat. Pub. No. 2010/0274188, now abandoned, which are incorporated by reference herein.

In some instances it may be desirable to dilate at least a portion of a Eustachian tube (26). For instance, as described above, in some circumstances a Eustachian tube (26) may become blocked or otherwise inflamed such that natural draining and ventilation of the middle ear (14) does not occur. In such circumstances, fluid buildup in the middle ear (14) may occur thus leading to chronic infection. While symptoms caused by such a blockage of the Eustachian tube (26) may be treated using procedures described above, treatment of the condition itself may still be desired. One such treatment may include the dilation of the Eustachian tube (26), thereby opening the Eustachian tube (26) to drain fluid from the middle ear (14) and restore natural functioning of the Eustachian tube (26). Examples of devices and methods that may be used to provide dilation of the Eustachian tube (26) are described in U.S. patent application Ser. No. 14/317,269, entitled "Vent Cap for a Eustachian Tube Dilation System," filed Jun. 29, 2014, issued as U.S. Pat. No. 10,350,396 on Jul. 16, 2019, the disclosure of which is incorporated by reference herein. Further examples are described in greater detail below.

II. Overview of Exemplary Methods of Treating Paranasal Sinuses

The paranasal sinuses are hollow cavities in the skull connected by small openings, also known as ostia, to the nasal cavity. Each ostium between a paranasal sinus and the nasal cavity is formed by bone covered by a layer of mucosal tissue. Normally, air passes into and out of the paranasal sinuses through the ostia. Also, mucus is continually formed by the mucosal lining of the sinuses and drains through the ostia and into the nasal cavity. Inflammation of one or more paranasal sinuses is generally referred to as sinusitis. If left untreated, chronic sinusitis may result in irreparable damage to the tissues and/or bony structures of the paranasal anatomy. The initial treatment of chronic sinusitis may involve the use of drugs such as decongestants, steroid nasal sprays, and antibiotics (if the infection is bacterial). In cases where drug treatment alone fails to provide permanent relief, surgical intervention may be indicated.

One kind of surgical procedure for treating chronic sinusitis is functional endoscopic sinus surgery (FESS). FESS is may be performed using an endoscope and various rigid instruments inserted through the patient's nostril. The endoscope is used to visualize the positioning and use of various rigid instruments used for removing tissue from the nasal cavity and sinus ostia in an attempt to improve sinus drainage.

A technique known as the Balloon Sinuplasty™ procedure and a system for performing the procedure has been developed by Acclarent Inc, of Menlo Park, Calif. for the treatment of sinusitis. A number of US patents and patent applications including U.S. Pat. No. 7,645,272, entitled "Devices, Systems and Methods for Treating Disorders of the Ear, Nose and Throat," issued Jan. 12, 2010, the disclosure of which is incorporated by reference herein; U.S. Pat. No. 7,654,997, entitled "Devices, Systems and Methods for Diagnosing and Treating Sinusitus and Other Disorders of the Ears, Nose and/or Throat," issued Feb. 2, 2010, the disclosure of which is incorporated by reference herein; and U.S. Pat. No. 7,803,150, entitled "Devices, Systems and Methods Useable for Treating Sinusitis," issued Sep. 28, 2010, the disclosures which is incorporated by reference herein, describe various example of the Balloon Sinuplasty™ procedure as well as various devices useable in the performance of such procedure. In the Balloon Sinuplasty™ procedure, a guide catheter is inserted into the nose and positioned within or adjacent to the ostium of the affected paranasal sinus. A guidewire is then advanced through the guide catheter and into the affected paranasal sinus. Thereafter, a dilation catheter having an expandable dilator (e.g. an inflatable balloon) is advanced over the guidewire to a position where the dilator is positioned within the ostium of the affected paranasal sinus. The dilator is then expanded, causing dilation of the ostium and remodelling of bone adjacent to the ostium, without required incision of the mucosa or removal of any bone. The catheters and guidewire are then removed and the dilated ostium allows for improved drainage from and ventilation of the affected paranasal sinus.

To at least some extent, similar exemplary systems and methods for treating the middle ear and Eustachian tube may also be used for treating the paranasal sinuses and vice versa. Furthermore, like afflictions of the middle ear and Eustachian tube, treatments have been developed for the paranasal sinuses, but have one or more shortcomings. Therefore, a need exists for improved methods and systems for accessing, diagnosing and treating target tissue regions within the paranasal sinuses. Ideally, such methods and systems would be minimally invasive and pose very little risk of damage to healthy ear tissue.

III. Overview of Exemplary Dilation Catheter System

As noted above, a Eustachian tube (26) may be treated by expanding a dilator within the Eustachian tube (26). Similarly, a sinus ostium or other passageway associated with drainage of a sinus cavity (e.g., a frontal recess) may be treated by expanding a dilator within the sinus ostium or other passageway. Since all of these anatomical structures may be accessed transnasally, it may be desirable to provide an instrument that is capable of dilating Eustachian tube (26), sinus ostia, and other passageways associated with drainage of a sinus cavity.

When using an instrument to dilate a Eustachian tube (26), where the instrument is inserted via the Eustachian tube ostium (28) at the nasopharynx (30), it may be desirable to ensure that the tip of the instrument does not traverse the isthmus (29). In particular, by preventing the instrument from traversing the isthmus (29), the instrument may be prevented from reaching the middle ear (14) where it may cause damage to anatomical structures therein. U.S. patent application Ser. No. 14/317,269, issued as U.S. Pat. No. 10,350,396 on Jul. 16, 2019, describes the incorporation of an enlarged tip on a dilation catheter that is used to dilate a Eustachian tube (26). The enlarged tip is small enough to allow the tip to pass through the Eustachian tube (26) in order to properly position a dilator in the Eustachian tube (26); but the enlarged tip is unable to pass through the isthmus (29). The enlarged tip thus arrests advancement of the instrument to prevent the instrument from reaching the middle ear.

To the extent that an enlarged tip is beneficial for a dilation catheter as used in Eustachian tube (26) dilation procedures, the same enlarged tip may render a dilation catheter inoperable for use in a sinus ostium/passageway dilation procedure. In particular, the enlarged tip may be too large to pass through a sinus ostium/passageway. Thus, it may not be possible to advance such a dilation catheter far enough for the dilator to be properly positioned in the sinus ostium/passageway.

Figure 7:
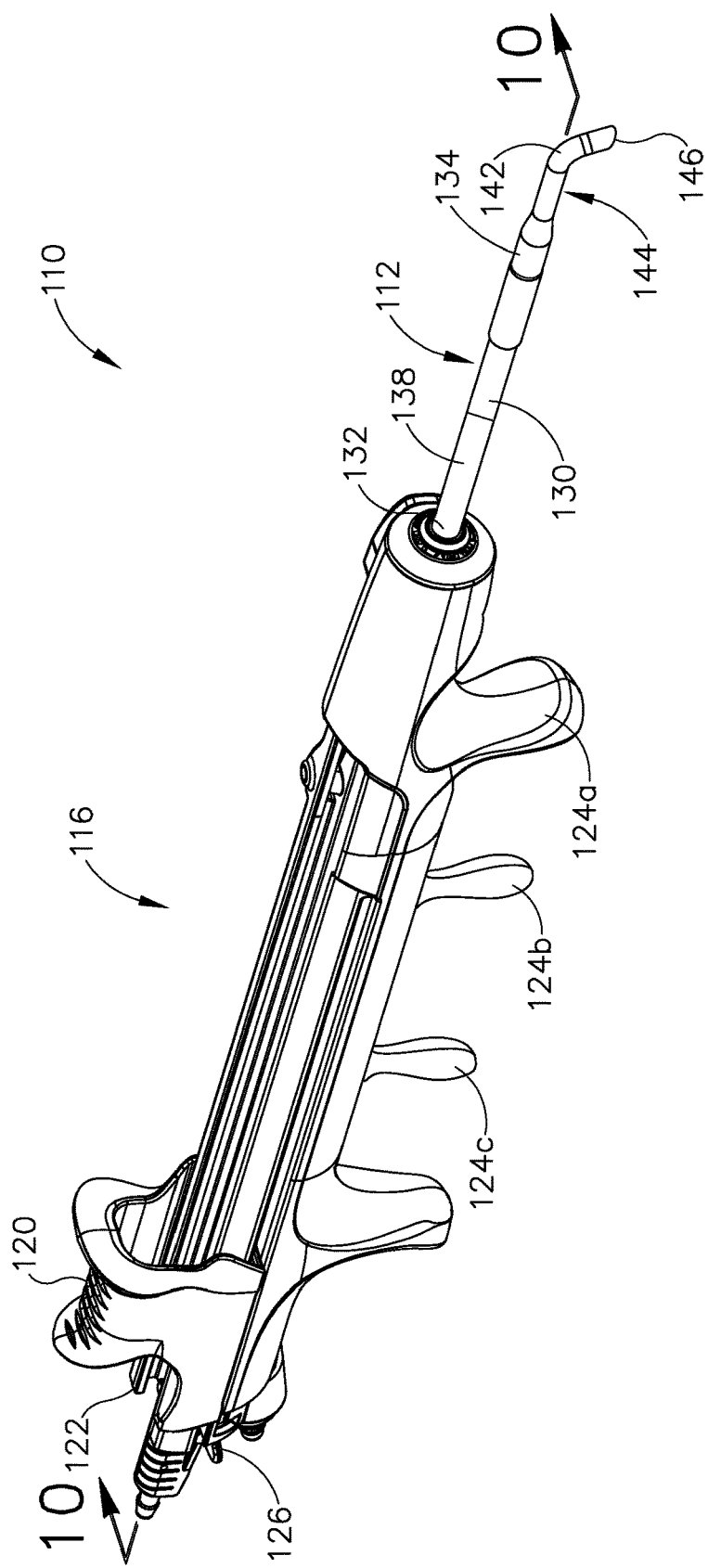
FIG. 7 depicts a perspective view of an exemplary dilation catheter system.
Figure 8:
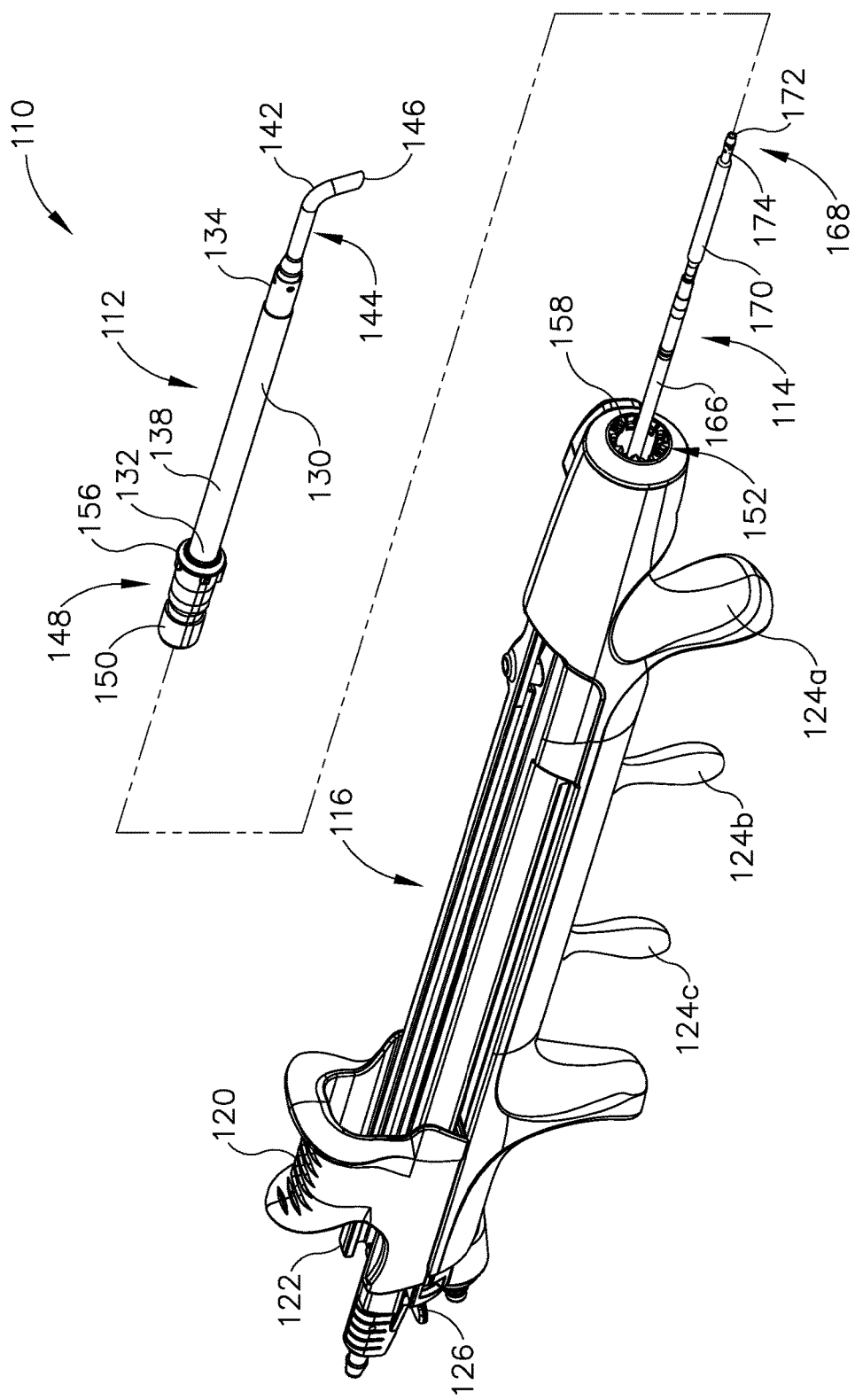
FIG. 8 depicts a partially disassembled perspective view of the dilation catheter system of FIG. 7.

FIGS. 7-14 show an exemplary instrument (110) that may be used to dilate the Eustachian tube (26), sinus ostia, and other passageways associated with drainage of a sinus cavity. As described in greater detail below, instrument (110) is configured to provide different distal tip configurations based on whether the instrument (110) is to be used to dilate a Eustachian tube (26) or a sinus ostium/passageway. As shown in FIGS. 7-8, instrument (110) of this example includes a guide catheter (112) and a balloon dilation catheter (114), which are together operable by a single hand grasping a handle (116). Various portions of instrument (110) may be constructed and operable in accordance with at least some of the teachings of U.S. Pub. No. 2012/0071856, entitled "Medical Device and Method for Treatment of a Sinus Opening," published Mar. 22, 2012, issued as U.S. Pat. No. 9,554,817 on Jan. 31, 2017, the disclosure of which is incorporated by reference herein.

The instrument (110) further includes a guide wire (not shown), a balloon catheter movement slider (120), a guidewire movement slider (122), and a suction pathway (not shown). The balloon catheter movement slider (120) is configured for advancement and retraction of the balloon dilation catheter (114) through the handle (116) and the guide catheter (112) by user operation of the balloon catheter movement slider (120) using a thumb or single finger. The handle (116) is ergonomically designed such that the finger anchoring pegs (124a, 124b, 124c) can be placed between the fingers of either a right handed or left handed user to provide for support of the instrument (110). Furthermore, a locking tab (126) restricts proximal movement of the balloon catheter movement slider (120) when tab (126) is in the up position; but allows for distal movement of slider (120). When the locking tab (126) is in the down position, the balloon dilation catheter (114) and the guidewire (not shown) can be inserted into the handle (116) through the guide catheter (112).

Figure 9:
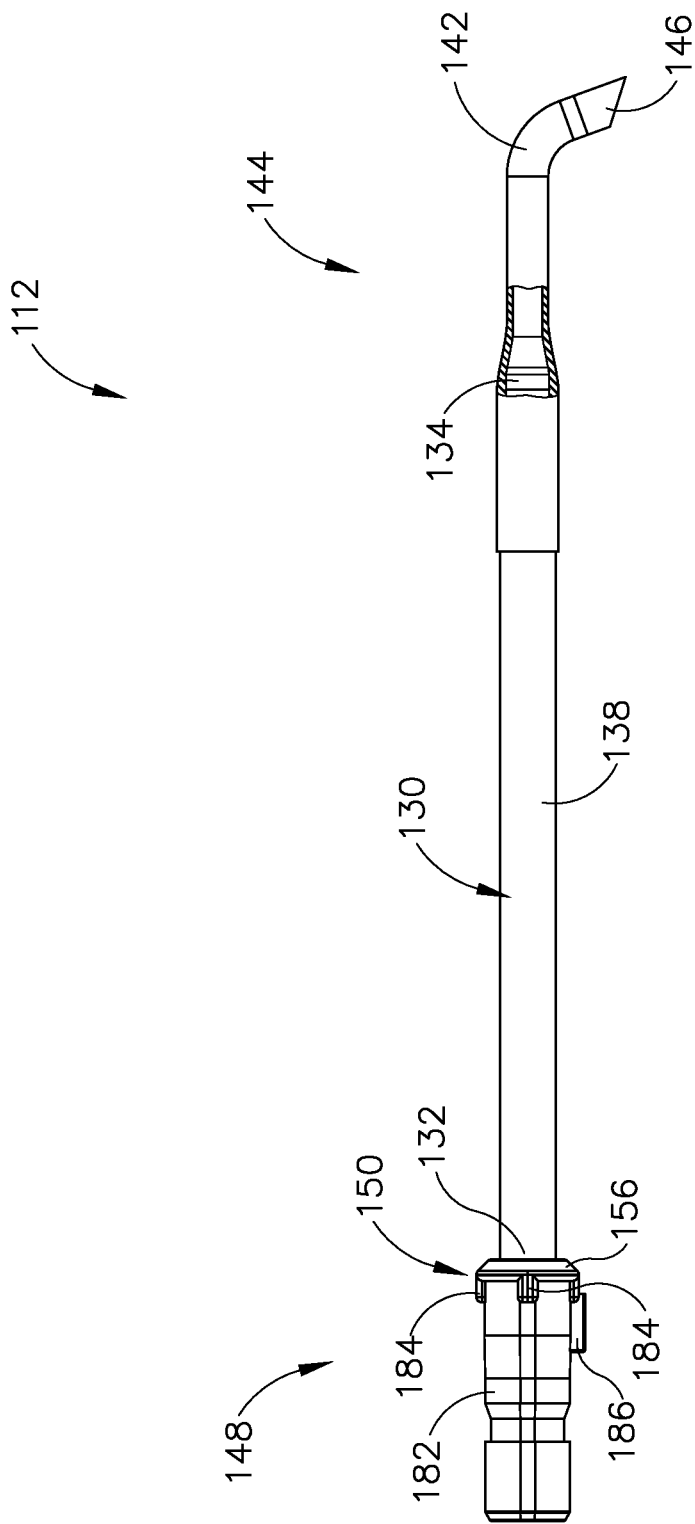
FIG. 9 depicts a side view of an exemplary guide catheter of the dilation catheter system of FIG. 7.
Figure 10:
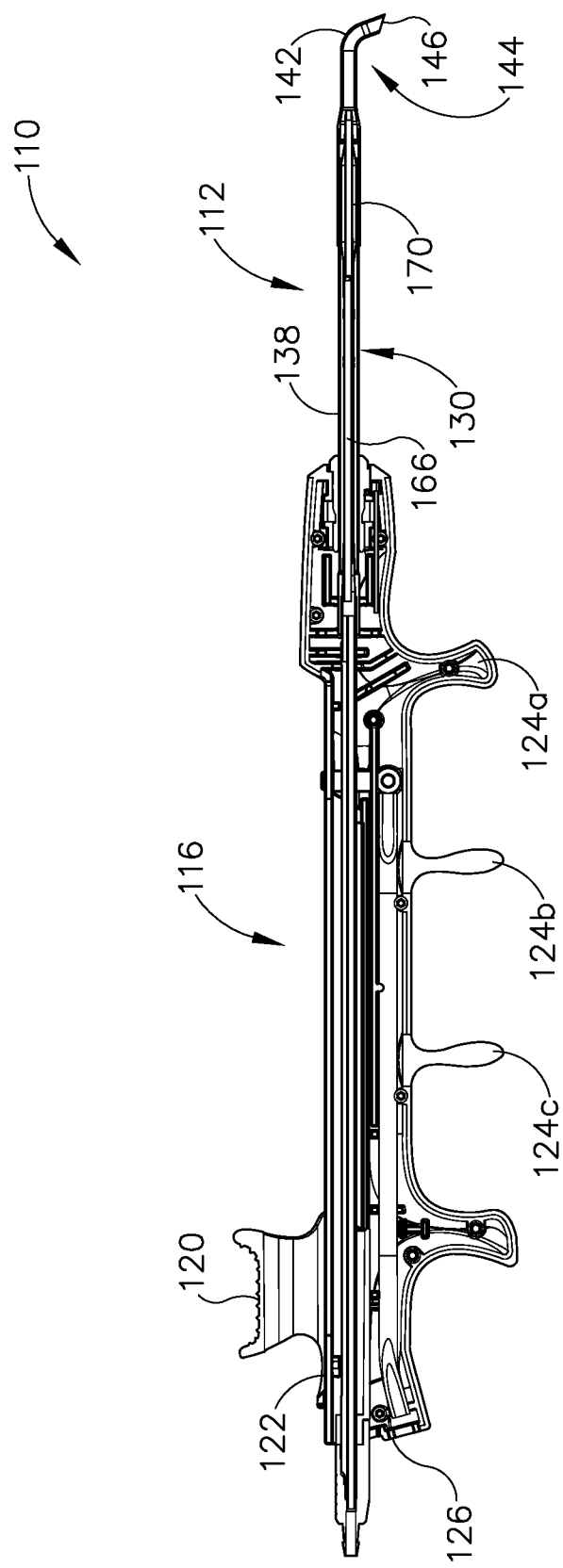
FIG. 10 depicts a cross-sectional view of the dilation catheter system of FIG. 7 taken along section line 10-10 of FIG. 7.

As best seen in FIGS. 8-9, the guide catheter (112) of the present example includes an elongate tubular shaft (130) that has a proximal end (132), a distal end (134), and a lumen (136) (see FIG. 11A) therebetween. The guide catheter (112) may have any suitable length, diameter, angle of bend, and location of the bend along the length of guide catheter (112), to facilitate accessing the Eustachian tube (26) (see FIG. 1). By way of example only, the guide catheter (112) may have a length between about 8 cm and about 20 cm, and more particularly between about 10 cm and about 15 cm, and in particular about 11 cm. Alternatively, any other suitable dimensions may be used.

The elongate tubular shaft (130) has an outer shaft tube (138), an inner shaft tube (140) (see FIG. 11A), and the lumen (136) (see FIG. 11A) therein. The outer shaft tube (138) may be constructed of a stiff material such as stainless steel and the inner shaft tube (140) may be constructed of a more flexible material such as a polymeric material including but not limited to nylon and further including a PTFE liner. By way of example only, the lumen (136) may have a diameter of between about 2 mm and 3 mm, and particularly between about 2.5 mm and 2.6 mm such that balloon dilation catheter (114) can be easily inserted into lumen (136) for dilation of the Eustachian tube (26) (see FIG. 1). Alternatively, any other suitable dimensions may be used.

The combination guide catheter (112) and balloon dilation catheter (114) make a compact system that is designed for a one-handed procedure. By way of example only, the length of the guide catheter (112) that is distal of a bend (142) in the guide catheter (112) may be between about 0.5 cm and 2.0 cm, or more particularly between about 1 and 2 cm, and in particular about 1 cm. This compactness may help reduce interference with other instruments, such as an endoscope (not shown) that may be used to help in visualizing the positioning of the system. Again, though, any other suitable dimensions may be used.

By way of example, a distal portion (144) of the guide catheter (112) may have a preformed bend (142) with an angle between about 45 degrees and about 65 degrees, and more particularly between about 50 degrees and about 60 degrees, and in particular about 55 degrees to facilitate access into the Eustachian tube (26) from within the nasopharynx (30). The distal portion (144) of the guide catheter (112) may be constructed of a transparent material such as a polymer including but not limited to nylon and PTFE such that balloon dilation catheter (114) is visible within the distal portion (144) and is more flexible than the elongate tubular shaft (130). A distal tip (146) of the distal portion (144) of the guide catheter (112) is made of polyether block amides (e.g., PEBAX® by Arkema) such that it provides for atraumatic access to the Eustachian tube (26) (see FIG. 1), and may contain 20% barium sulfate or other similar radiopaque materials for visualizable access.

Figure 11A:
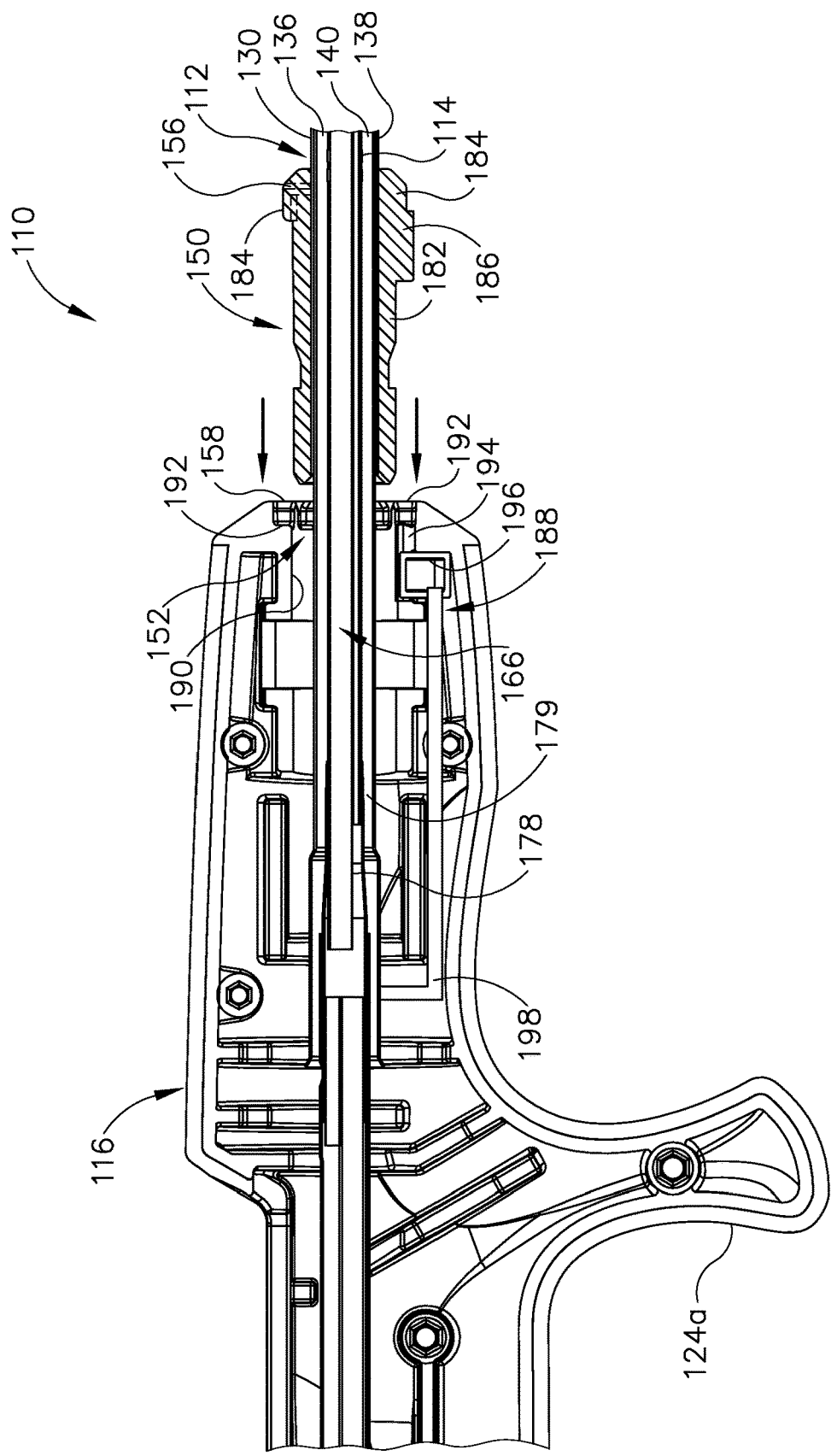
FIG. 11A depicts an enlarged cross-sectional view of an intermediate portion of the dilation catheter system of FIG. 7, with the guide catheter of FIG. 9 partially disassembled from a remainder of the dilation catheter system.
Figure 11B:
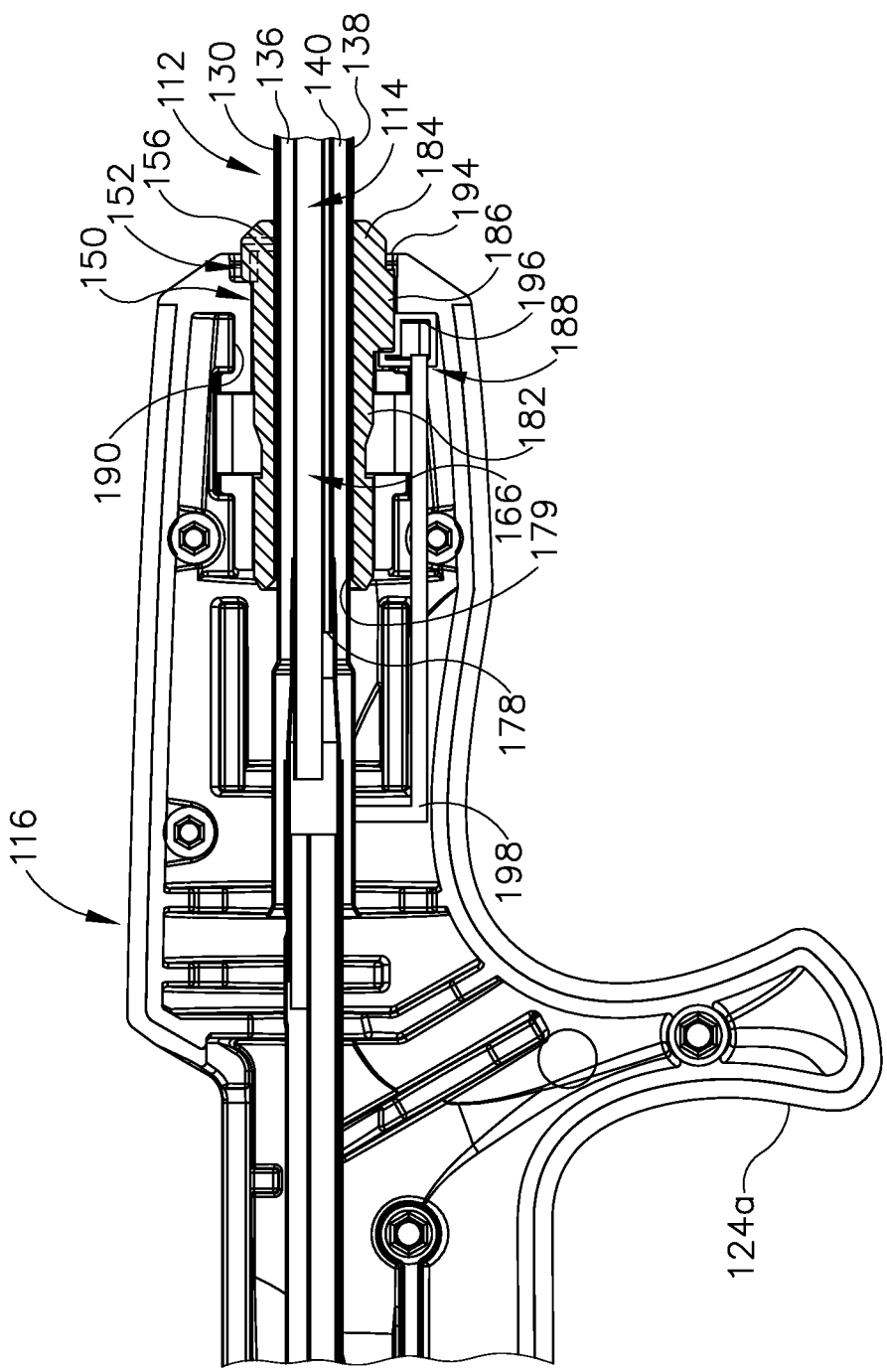
FIG. 11B depicts an enlarged cross-sectional view of an intermediate portion of the dilation catheter system of FIG. 7, with the guide catheter fully assembled with the remainder of the dilation catheter system.

As best seen in FIGS. 8 and 11A-11B, a proximal portion (148) of the guide catheter (112) includes a proximal, activation hub (150) to aid in insertion of the balloon dilation catheter (114) into a guide port (152) of the handle (116) of the instrument (110). To this end, the activation hub (150) is configured for being received and secured within the guide port (152). The activation hub (150) may be inserted into the guide port (152) until a distal, annular shoulder (156) abuts against an engagement surface (158) of the guide port (152). The activation hub (150) is ergonomically designed for insertion, location, and rotation with slight manipulations using a single hand.

The balloon dilation catheter (114) received within the guide catheter (112) generally includes an elongate shaft (166) having a proximal end (not shown) and a distal end portion (168). The balloon dilation catheter (114) further includes a dilation balloon (170) on the distal end portion (168) of the elongate shaft (166). For example, the dilation balloon (170) may be a polymer balloon (compliant, semi-compliant or non-compliant). In some versions, the dilation balloon (170) may be a suitable non-compliant material such as but not limited to polyethylene terepthalate (PET), PEBAX®, nylon or the like. The balloon dilation catheter (114) may include any size of dilation balloon (170) including but not limited to balloons of 2 mm to 8 mm in diameter, or of between about 5 mm and 6 mm (when inflated) and 12 mm to 24 mm in working length (for example 2 mm×12 mm, 3.5 mm×12 mm, 5 mm×16 mm, 5 mm×24 mm, 6 mm×16 mm, 6 mm×20 mm, 6 mm×24 mm, 7 mm×16 mm and 7 mm×24 mm). It will be appreciated that the balloon dilation catheter (114) generally includes a proximally located connection (not shown) for inflating/activating the dilation balloon (170).

The dilation balloon (170) may be expanded to dilate the Eustachian tube (26) (see FIG. 1) after it is placed in a desired location therein. Alternatively, the dilation balloon (170) may be expanded to dilate a sinus ostium or other passageway. In the context of Eustachian tube (26) dilation, the balloon dilation catheter (114) may be advanced to position the dilation balloon (170) in the Eustachian tube (26) via the pharyngeal ostium (28). An endoscope (not shown) may be used to assist in positioning balloon dilation catheter (114). The endoscope (not shown) may be advanced through the nasal passage to view the balloon dilation catheter (114). For example, a marker (not shown) on the elongate shaft (166) of the balloon dilation catheter (114) can be viewed from the endoscope to approximate a location of the dilation balloon (170) relative to the pharyngeal ostium (28) of the Eustachian tube (26) based on a distance of the marker (not shown) from the dilation balloon (170). Accordingly, the balloon dilation catheter (112) can be moved to a desired location before expansion of the dilation balloon (170) in the Eustachian tube (26). By way of example only, the endoscope (not shown) may be configured in accordance with at least some of the teachings of U.S. Pat. Pub. No. 2010/0030031, entitled "Swing Prism Endoscope," published Feb. 4, 2010, now abandoned, the disclosure of which is incorporated by reference herein. In some versions, the endoscope (not shown) is configured similar to the Acclarent Cyclops™ Multi-Angle Endoscope by Acclarent, Inc. of Menlo Park, Calif. Other suitable forms that the endoscope (not shown) may take will be apparent to those of ordinary skill in the art in view of the teachings herein.

The distal end portion (168) of the balloon dilation catheter (114) further includes a stop element in the form of a tip balloon (172). A flexible distal shaft end (174) that is constructed of a polymeric material (e.g., PEBAX®, etc.) extends from the distal end of dilation balloon (170) to tip balloon (172). Tip balloon (172) is fluidly isolated from dilation balloon (170), such that balloons (170, 172) may be selectively inflated and deflated independently relative to each other. For instance, dilation balloon (170) may be selectively inflated and deflated using a conventional inflator device (e.g., a syringe, any of the inflator devices described in any of the various references cited herein, etc.). In the present example, tip balloon (172) is inflated by a reservoir bulb (196) as will be described in greater detail below. FIG. 8 shows tip balloon (172) is in a deflated state. However, as will be described in additional detail below, the tip balloon (172) is configured to inflate from the deflated state (FIG. 12A) to an inflated state (FIG. 12B). In the deflated state, tip balloon (172) is sized to pass through a sinus ostium. In the inflated state, tip balloon (172) forms a bulbous stop element that is sized to arrest movement of balloon dilation catheter (114) at the isthmus (29) of a Eustachian tube (26).

In the present example, tip balloon (172) is atraumatic and about 1.5 mm to 2 mm in length with an outer diameter of between about 2 mm and 3 mm when tip balloon (172) is in the inflated state. The smoothness and roundness of the tip balloon (172) facilitates advancement of the balloon dilation catheter (114) by helping it glide smoothly through the Eustachian tube (26) (see FIG. 1). The inflated tip balloon (172) further acts as a safety stop. Specifically, in some patients the isthmus (29) (see FIG. 1) of the Eustachian tube (26) (see FIG. 1), is approximately 1 mm in diameter. Thus, the diameter of the inflated tip balloon (172) is larger than an outer diameter (177) (see FIG. 12B) of the distal shaft end (174) such that the size of the tip balloon (172) will inhibit the balloon dilation catheter (114) from passing through the isthmus (29) (see FIG. 1) and into the middle ear (14).

When the dilation balloon (170) is positioned in the Eustachian tube (26) and then inflated, the inflated dilation balloon (170) may be held in location for an extended period of time (e.g., several seconds or minutes). The balloon dilation catheter (114) may also deliver a substance to the Eustachian tube (26), such as one or more of the therapeutic or diagnostic agents described herein. The dilation balloon (170) may also carry an expandable stent (not shown) for delivery into the Eustachian tube (26) upon expansion of the dilation balloon (170). The balloon dilation catheter (114) and the guide catheter (112) may be removed from the patient after the dilation balloon (170) has been deflated/unexpanded. The Eustachian tube (26) may then resume functioning, normally opening and closing to equalize atmospheric pressure in the middle ear (14), allowing for drainage of fluid from the middle ear (14), and protecting the middle ear (14) from unwanted pressure fluctuations and loud sounds.

In use, the guide catheter (112) may be advanced into a nostril and through a nasal cavity to position distal tip (146) end of the guide catheter (112) at or near the ostium (28) of the Eustachian tube (26). In some versions, the guide catheter (112) may be passed through the nostril to the Eustachian tube (26) on the ipsilateral (same side) of the head. In some other versions, the guide catheter (112) may be passed through the nostril to the Eustachian tube (26) on the contralateral (opposite side) of the head. A guiding element, such as the guidewire (not shown) or illuminating fiber may be used to aid in accessing the Eustachian tube (26).

After the guide catheter (112) is in a desired position, the balloon catheter (114) is advanced through the guide catheter (112) to position the dilation balloon (170) of the balloon dilation catheter (114) within the Eustachian tube (26). The physician/user may place the index and middle fingers on the finger anchoring pegs (124a, 124b, 124c) and manipulate balloon catheter movement slider (120) and the guidewire movement slider (122) accordingly to slide the balloon dilation catheter (114) through the guide catheter (112) to position the dilation balloon (170) into a desired position within the Eustachian tube (26). However, it will be appreciated that other devices and methods may be used for positioning the dilation balloon (170) within the Eustachian tube (26). In any case, the inflated tip balloon (172) prevents the balloon dilation catheter (114) from crossing the isthmus (29) to reach the middle ear (14). Following placement of the balloon dilation catheter (114) into the desired position, any number of procedures may be carried out.

As shown in FIG. 11A, the elongate shaft (166) of the balloon dilation catheter (114) contains a dilation balloon lumen (178) (see FIG. 11A) and a tip balloon lumen (179) (see FIG. 11A). By adjacent dual lumen tubing, it is intended that the lumens are next to each other but are spaced apart from each other. The dilation balloon lumen (178) extends through the balloon dilation catheter (114) and fluidly connects to the dilation balloon (170) for inflating the dilation balloon (170) with a fluid, such as water, contrast medium, or saline through an inflation port (not shown) to a pressure of between about 3 and 15 atmospheres, or of between about 6 and 12 atmospheres. The tip balloon lumen (179) extends through the balloon dilation catheter (114) and fluidly connects to the tip balloon (172) for inflating the tip balloon (172) with a fluid, such as water, contrast medium, saline, nitrogen, oxygen, etc.

An injection lumen (not shown) may be provided to permit the optional injection of water, medicament, or even the introduction of another guidewire (not shown) through an injection port (not shown) at the proximal end of handle (116). It may be desirable to inject solutions containing contrast agents, pharmaceutically acceptable salt or dosage form of an antimicrobial agent (e.g. antibiotic, antiviral, anti-parasitic, antifungal, etc.), an anesthetic agent with or without a vasoconstriction agent (e.g. Xylocaine with or without epinephrine, Tetracaine with or without epinephrine, etc.), an analgesic agent, a corticosteroid or other anti-inflammatory (e.g. an NSAID), a decongestant (e.g. vasoconstrictor), a mucus thinning agent (e.g. an expectorant or mucolytic), a surfactant, an agent that prevents or modifies an allergic response (e.g. an antihistamine, cytokine inhibitor, leucotriene inhibitor, IgE inhibitor, immunomodulator), an allergen or another substance that causes secretion of mucous by tissues, hemostatic agents to stop bleeding, antiproliferative agents, cytotoxic agents (e.g. alcohol), biological agents such as protein molecules, stem cells, genes or gene therapy preparations, or the like.

Some nonlimiting examples of antimicrobial agents that may be used include acyclovir, amantadine, aminoglycosides (e.g., amikacin, gentamicin and tobramycin), amoxicillin, amoxicillinlclavulanate, amphotericin B, ampicillin, ampicillinlsulbactam, atovaquone, azithromycin, cefazolin, cefepime, cefotaxime, cefotetan, cefpodoxime, ceflazidime, ceflizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscamet, ganciclovir, atifloxacin, imipenemlcilastatin, isoniazid, itraconazole, ketoconazole, metronidazole, nafcillin, nafcillin, nystatin, penicillin, penicillin G, pentamidine, piperacillinitazobactam, rifampin, quinupristindalfopristin, ticarcillinlclavulanate, trimethoprimlsulfamethoxazole, valacyclovir, vancomycin, mafenide, silver sulfadiazine, mupirocin (e.g., Bactroban, Glaxo SmithKline, Research Triangle Park, N.C.), nystatin, triamcinolonelnystatin, clotrimazolelbetamethasone, clotrimazole, ketoconazole, butoconazole, miconazole, tioconazole, detergent-like chemicals that disrupt or disable microbes (e.g., nonoxynol-9, octoxynol-9, benzalkonium chloride, menfegol, and N-docasanol); chemicals that block microbial attachment to target cells and/or inhibits entry of infectious pathogens (e.g., sulphated and sulphonated polymers such as PC-515 (carrageenan), Pro-2000, and Dextrin 2 Sulphate); antiretroviral agents (e.g., PMPA gel) that prevent retroviruses from replicating in the cells; genetically engineered or naturally occurring antibodies that combat pathogens such as anti-viral antibodies genetically engineered from plants known as "plantibodies;" agents which change the condition of the tissue to make it hostile to the pathogen (such as substances which alter mucosal pH (e.g., Buffer Gel and Acid form); non-pathogenic or "friendly" microbes that cause the production of hydrogen peroxide or other substances that kill or inhibit the growth of pathogenic microbes (e.g., *lactobacillus*); antimicrobial proteins or peptides such as those described in U.S. Pat. No. 6,716,813, entitled "Use of Antimicrobial Proteins and Peptides for the Treatment of Otitis Media and Paranasal Sinusitis," issued Apr. 6, 2004, the disclosure of which is incorporated by reference herein, or antimicrobial metals (e.g., colloidal silver).

Additionally or alternatively, in some applications where it is desired to treat or prevent inflammation the substances delivered may include various steroids or other anti-inflammatory agents (e.g., nonsteroidal anti-inflammatory agents or NSAIDS), analgesic agents or antipyretic agents. For example, corticosteroids that have previously administered by intranasal 10 administration may be used, such as beclomethasone (Vancenase® or Beconase), flunisolide (Nasalid®), fluticasone proprionate (Flonase®), triamcinolone acetonide (Nasacort®), budesonide (Rhinocort Aqua®), loterednol etabonate (Locort) and mometasone (Nasonex®). Other salt forms of the aforementioned corticosteroids may also be used. Also, other non-limiting examples of steroids that may be useable include but are not limited to aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexarnethasone and methylprednisolone. Other anti-inflammatory, analgesic or antipyretic agents that may be used include the nonselective COX inhibitors (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and Selective COX-2 Inhibitors (e.g., diaryl-substituted furanones such as rofecoxib; diaryl-substituted pyrazoles such as celecoxib; indole acetic acids such as etodolac and sulfonanilides such as mmesulide).

Additionally or alternatively, in some applications, such as those where it is desired to treat or prevent an allergic or immune response and/or cellular proliferation, the substances delivered may include: various cytokine inhibitors such as humanized anti-cytokine antibodies, anti-cytokine receptor antibodies, recombinant (new cell resulting from genetic recombination) antagonists, or soluble receptors; various leucotriene modifiers such as zafirlukast, montelukast and zileuton; immunoglobulin E (IgE) inhibitors such as Omalizumab (an anti-IgE monoclonal antibody formerly called rhu Mab-E25) and secretory leukocyte protease inhibitor); and SYK Kinase inhibitors such as an agent designated as "R-112" manufactured by Rigel Pharmaceuticals, Inc, South San Francisco, Calif.

Additionally or alternatively, in some applications, such as those where it is desired to shrink mucosal tissue, cause decongestion, or effect hemostasis, the substances delivered may include various vasoconstrictors for decongestant and or hemostatic purposes including but not limited to pseudoephedrine, xylometazoline, oxymetazoline, phenylephrine, epinephrine, etc.

Additionally or alternatively, in some applications, such as those where it is desired to facilitate the flow of mucous, the substances delivered may include various mucolytics or other agents that modify the viscosity or consistency of mucous or mucoid secretions, including but not limited to acetylcysteine. In one particular embodiment, the substance delivered may comprise a combination of an anti-inflammatory agent (e.g. a steroid or an NSAID) and a mucolytic agent.

Additionally or alternatively, in some applications such as those where it is desired to prevent or deter histamine release, the substances delivered may include various mast cell stabilizers or drugs which prevent the release of histamine such as cromolyn (e.g., Nasal Chroma) and nedocromil.

Additionally or alternatively, in some applications such as those where it is desired to prevent or inhibit the effect of histamine, the substances delivered may include various antihistamines such as azelastine (e.g., Astylin) diphenhydramine, loratidine, etc.

Additionally or alternatively, in some embodiments such as those where it is desired to dissolve, degrade, cut, break or remodel bone or cartilage, the substances delivered may include substances that weaken or modify bone and/or cartilage to facilitate other procedures wherein bone or cartilage is remodeled, reshaped, broken or removed. One example of such an agent would be a calcium chelator such as EDTA that could be injected or delivered in a substance delivery implant next to a region of bone that is to be remodeled or modified. Another example would be a preparation consisting of or containing bone degrading cells such as osteoclasts. Other examples would include various enzymes of material that may soften or break down components of bone or cartilage such as collagenase (CGN), trypsin, trypsin1LEDTA, hyaluronidase, and tosyllysylchloromethane (TLCM).

Additionally or alternatively, in some applications such as those wherein it is desired to treat a tumor or cancerous lesion, the substances delivered may include antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as; alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other antitumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase inhibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-I, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, 1MC-IC11, 1M862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000) which is expressly incorporated herein by reference, biological response modifiers (e.g., interferon, bacillus calmetteguerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, fluorouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogslcongeners and derivatives of such compounds as well as other antitumor agents not listed here.

Additionally or alternatively, in some applications such as those where it is desired to grow new cells or to modify existing cells, the substances delivered may include cells (mucosal cells, fibroblasts, stem cells or genetically engineered cells) as well as genes and gene delivery vehicles like plasmids, adenoviral vectors or naked DNA, mRNA, etc. injected with genes that code for anti-inflammatory substances, etc., and, as mentioned above, osteoclasts that modify or soften bone when so desired, cells that participate in or effect mucogenesis or ciliagenesis, etc.

In some instances, a local anesthetic, such as Lidocaine is injected through an injection lumen (not shown) prior to dilation of the Eustachian tube (26). The injection lumen (not shown) can be used for venting during dilation so that pressure in the middle ear (14) does not increase or decrease in response to positioning and inflation of dilation balloon (170) within the Eustachian tube (26).

IV. Exemplary Handle and Guide Catheter having an Activation Hub

FIGS. 9-11A show one example of the handle (116), the tip balloon (172), and the guide catheter (112) having the activation hub (150) configured to trigger inflation of the tip balloon (172). The activation hub (150), like the elongate tubular shaft (130) distally extending therefrom, is generally hollow and configured to receive the balloon dilation catheter (114) therethrough. The activation hub (150) is more particularly configured to removably secure within the guide port (152) while simultaneously triggering inflation of the tip balloon (172). In order to secure the guide catheter (112) to the handle (116), the activation hub (150) includes a hub body (182) having a plurality of ribs (184) longitudinally and radially therealong toward the distally positioned annular shoulder (156). The plurality of ribs (184) generally provide for angular alignment of the guide catheter (112) relative to the handle (116), whereas the annular shoulder (156) is configured to halt further insertion of the activation hub (150) into the handle (116) beyond the annular shoulder (156). Furthermore, the activation hub (150) notably includes an engagement tab (186) extending longitudinally along a portion of the hub body (182) and transversely beyond the ribs (184) for engaging a fluid supply assembly (188) within the handle (116) as shown in FIGS. 11A-11B. It will be appreciated that the guide catheter (112) may be further secured within the handle (116) by friction or a latch (not shown), such as a mechanical latch, a magnetic latch, and/or an electromechanical latch, detents, and/or any other suitable features for removably securing the activation hub (150).

FIG. 11A shows the guide catheter (112) coaxially aligned with the balloon dilation catheter (114) while being inserted into the guide port (152) of the handle (116). The guide port (152) includes a bore (190) and plurality of grooves (192) extending longitudinally and radially beyond the bore (190). The bore (190) receives the hub body (182), while the plurality of grooves (192) respectively corresponds to the plurality of ribs (184) for angular alignment of the activation hub (150). In addition, the guide port (152) also includes a slot (194) configured to receive the engagement tab (186) of the activation hub (150). The slot (194) extends proximally through the handle (116) from the guide port (152) to a reservoir bulb (196) of the fluid supply assembly (188). Thus, as the engagement tab (186) is inserted into the slot (194), the engagement tab (186) compresses the reservoir bulb (196) in order to discharge the fluid contained therein from the reservoir bulb (196), as shown in FIG. 11B.

In the present example, the fluid supply assembly (188) further includes a supply tube (198) fluidly connected to the reservoir bulb (196) to receive the fluid discharged from the reservoir bulb (196) during compression by engagement tab (186). The supply tube (198) extends proximally from the reservoir bulb (196) through the handle (116) and is configured to align and fluidly seal with a proximal portion of the tip balloon lumen (179). Thereby, the supply tube (198) fluidly communicates the fluid discharged from the reservoir bulb (196) to the tip balloon lumen (179) and toward the tip balloon (172) for inflation as shown in FIG. 12B. It should therefore be understood that reservoir bulb (196), supply tube (198), tip balloon lumen (179), and tip balloon (172) together form a closed fluid circuit.

Figure 12A:
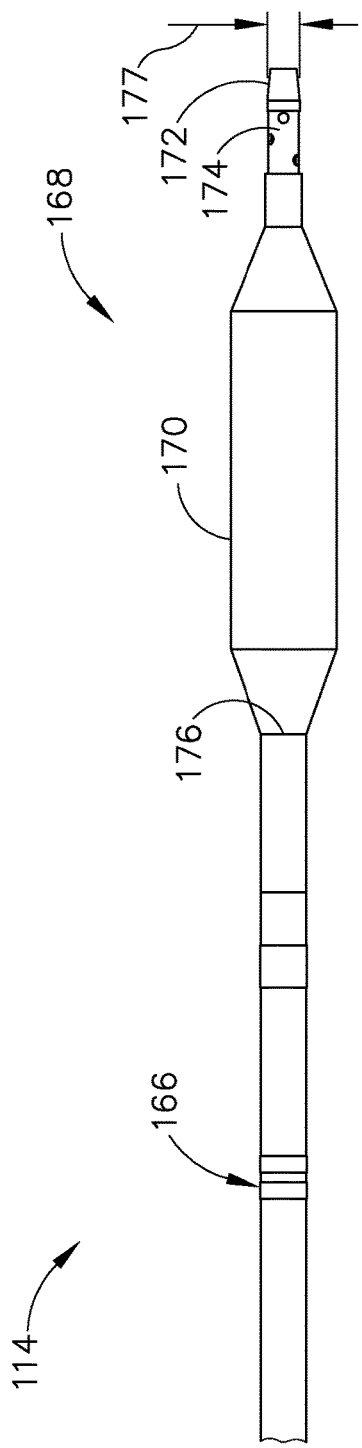
FIG. 12A depicts an enlarged side view of the distal end of a dilation catheter of the dilation catheter system of FIG. 7, with a dilator of the dilation catheter in an inflated state and a tip of the dilation catheter in a deflated state.
Figure 12B:
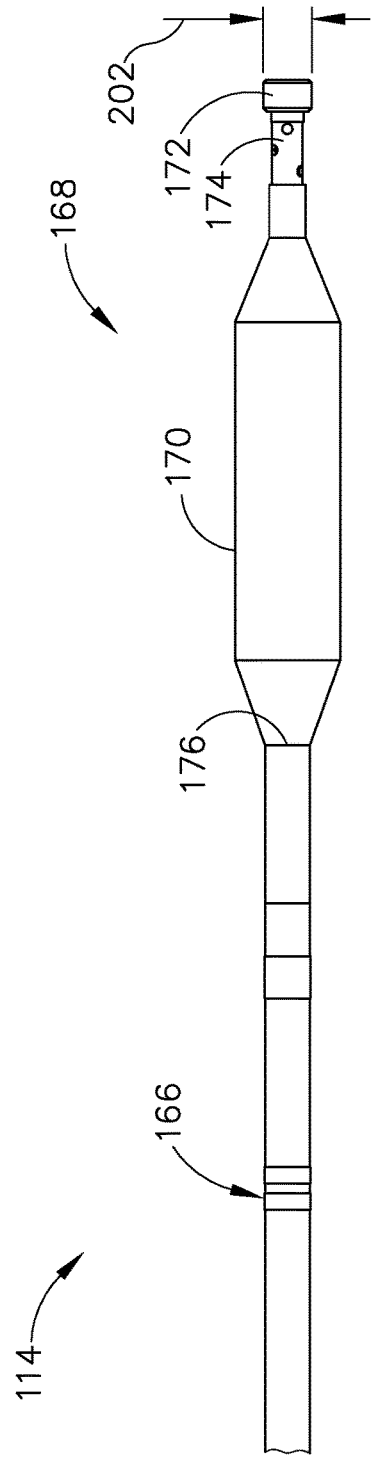
FIG. 12B depicts an enlarged side view of the distal end of a dilation catheter of the dilation catheter system of FIG. 7, with the dilator in the inflated state and the tip in an inflated state.

FIG. 12A shows the tip balloon (172) in a contracted state, whereas FIG. 12B shows the tip balloon (172) in an expanded state after having received the fluid from the tip balloon lumen (179). To this end, the tip balloon lumen (179) extends through the dilation balloon (170) and to the inflatable tip balloon (172) positioned on the distal shaft end (174), which defines the outer shaft diameter (177). The tip balloon (172) in the contracted state defines a contracted outer diameter generally equivalent to the outer shaft outer diameter for insertion through relatively tight spaces (e.g., sinus ostia) within the patient. Upon receiving the fluid for inflation, the exemplary tip balloon (172) projects radially outwardly from the distal shaft end (174) to define an expanded outer diameter (202) that is larger than the outer shaft diameter for preventing the balloon dilation catheter (114) from advancing to an undesirable position within the patient, such as beyond the isthmus (29). It should also be understood that, in some versions, an alternative tip (not shown) may inflate radially inwardly from the distal shaft end (174) for inhibiting the guidewire (not shown) from advancing to an undesirable position within the patient. Another example may include yet another alternative tip (not shown) that inflates both radially inwardly and radially outwardly from the distal shaft end (174). While the tip balloon (172) is generally cylindrical, it will be appreciated that the tip balloon (172) may be configured to inflate to any desirable shape, such as a blueberry shape. Thus, the tip balloon (172) is not intended to be unnecessarily limited to the shape shown and described herein.

With respect to FIGS. 11A-12B, the tip balloon (172) may be deflated, as shown in one example, by removing the guide catheter (112) from the guide port (152). More particularly, in some versions the reservoir bulb (196) is resilient and, as such, will generally self-expand from the compressed state (FIG. 11B) to its original, uncompressed state (FIG. 11A). Thereby, removing the guide catheter (112) from the guide port (152) disengages the engagement tab (186) from the reservoir bulb (196) and causes the reservoir bulb (196) to expand. This expansion of reservoir bulb (196) draws the fluid from the tip balloon (172) until the pressure equalizes and the tip balloon (172) returns to its contracted state. As an alternative to the vacuum or in addition to forming reservoir bulb (196) of a resilient material that is biased to assume the expanded configuration shown in FIG. 11A, the tip balloon (172) may be configured to be selectively withdrawn into the elongate shaft (166) to compress the tip balloon (172) and force the fluid back to the reservoir bulb (196). As yet another merely illustrative example, tip balloon (172) may be formed of a resilient material that is biased to assume the configuration shown in FIG. 12B. Thus, as soon as engagement tab (186) relieves pressure by disengaging reservoir bulb (196), the resilience of tip balloon (172) may drive the fluid from tip balloon (172) back to reservoir bulb (196). Of course, it will be appreciated that other features and methods for contracting the tip balloon (172) from its expanded state may be used, and, as such, the invention described herein is not intended to be limited to contracting via the vacuum.

V. Exemplary Sinuplasty Guide Catheter Set

Figure 13:
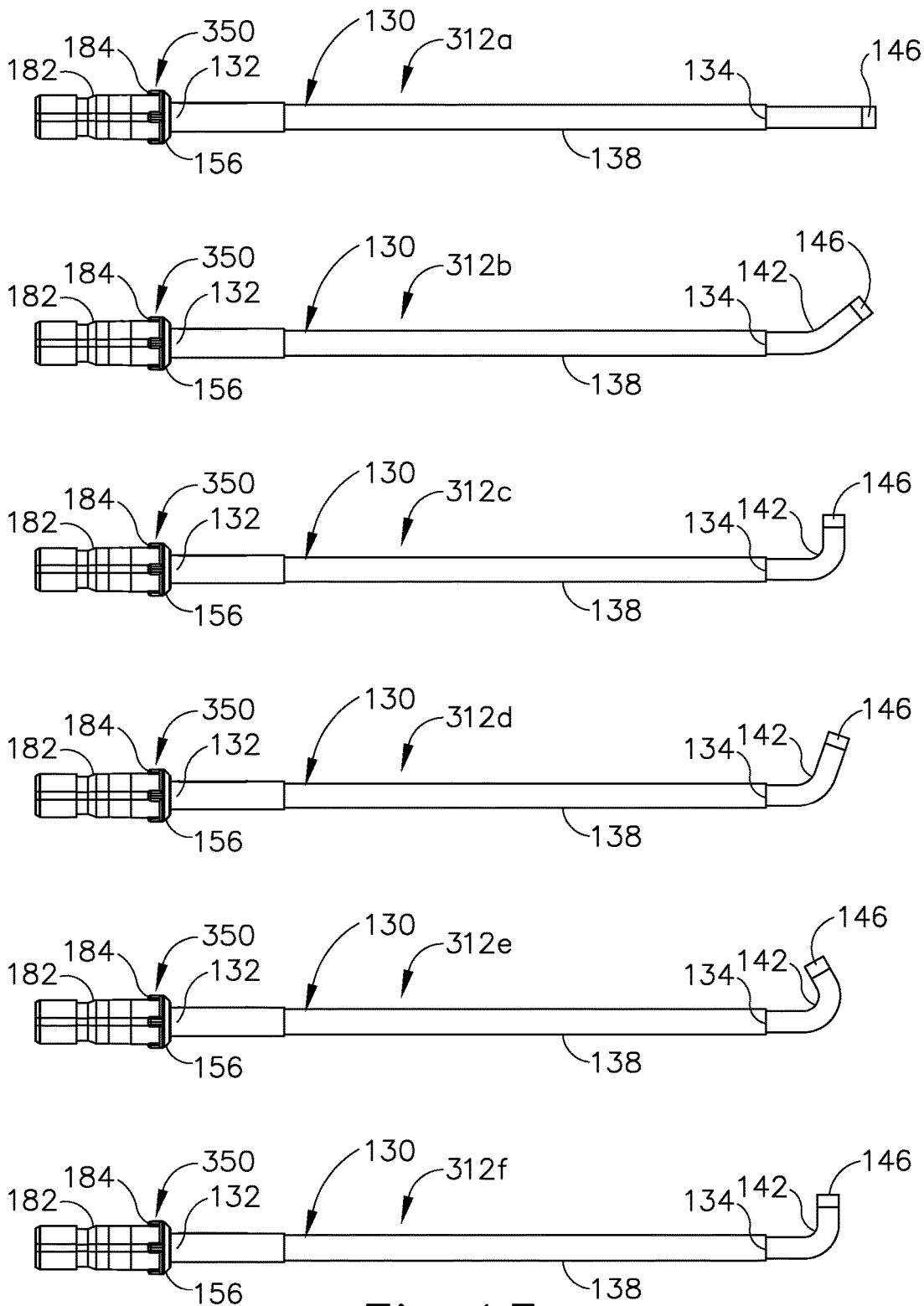
FIG. 13 depicts a collection of additional exemplary guide catheters that may be used with the dilation catheter system of FIG. 7, with a plurality of respective angles useful for positioning a balloon dilation catheter.

FIG. 13 shows a set of sinus guide catheters (312*a*, 312*b*, 312*c*, 312*d*, 312*e*, 312*f*) that may be used in conjunction with the instrument (110) for dilating ostia and other drainage passageways of different sinuses. Each of these guide catheters (312*a*, 312*b*, 312*c*, 312*d*, 312*e*, 312*f* has a substantially rigid proximal section, a less rigid distal section, an atraumatic tip, and a preformed bend in the distal section. In particular, guide catheter (312*a*) has a preformed bend defining a bend angle of approximately 0 degrees, guide catheter (312*b*) has a preformed bend defining a bend angle of approximately 30 degrees, guide catheters (312*c*, 312*f* have a preformed bend defining a bend angle of approximately 90 degrees, guide catheter (312*d*) has a preformed bend defining a bend angle of approximately 70 degrees, and guide catheter (312*e*) has a preformed bend defining a bend angle of approximately 110 degrees. Of course, these bend angles are just merely illustrative examples. The guide catheters (312*a*, 312*b*, 312*c*, 312*d*, 312*e*, 312*f* may have different diameters in the less rigid distal section such as shown in with regard to guide catheters (312*c*, 312*f*).

Different distal end curvatures are useable to access the ostia or other drainage passageways of different sinuses. For example, a 70 degree guide catheter (312*d*) may be used to access the frontal recess, a 90 or 110 degree guide catheter (312*e*) may be used to access the ostium of a maxillary sinus, etc. Each of these guide catheters (312*a*, 312*b*, 312*c*, 312*d*, 312*e*, 312*f*) has an axial length of about 12.7 cm in the present example, though it should be understood that any other suitable lengths may be used.

By way of example only, these sinus guide catheters (312*a*, 312*b*, 312*c*, 312*d*, 312*e*, 312*f*) may be constructed and operable in accordance with at least some of the teachings of U.S. Pub. No. 2006/0004323, entitled "Apparatus and Methods for Dilating and Modifying Ostia of Paranasal Sinuses and Other Intranasal or Paranasal Structures," published Jan. 5, 2006, now abandoned, the disclosure of which is incorporated by reference herein; U.S. Pat. No. 8,894,614, entitled "Devices, Systems, and Methods Useable for Treating Frontal Sinusitis," issued Nov. 25, 2014, the disclosure of which is incorporated by reference herein; U.S. Pat. No. 7,654,997, the disclosure of which is incorporated by reference herein; and/or U.S. Pat. No. 7,803,150, the disclosure of which is incorporated by reference herein. The following description refers to sinus guide catheter (312*a*), but it should be understood that any of the other guide catheters (312*b*, 312*c*, 312*d*, 312*e*, 312*f*) of FIG. 13 may be similarly used. In addition, like numbers below indicate like features described above.

Given the relatively small size of sinus ostia as well as the path for sinus treatment, the guide catheter (312*a*) is configured for use with the balloon dilation catheter (114) described above but with the guide catheter (312*a*) having a deactivation hub (350) configured to prevent inflation of the tip balloon (172). The deactivation hub (350), like the elongate tubular shaft (130) distally extending therefrom, is generally hollow and configured to receive the balloon dilation catheter (114) therethrough. The deactivation hub (350) is also configured to removably secure within the guide port (152). In order to secure the guide catheter (112) to the handle (116), the deactivation hub (350) includes the hub body (182) having the plurality of ribs (184) and the annular shoulder (156), as described above. However, as shown in FIGS. 13-14, the deactivation hub (350) does not include the engagement tab (186) (see FIG. 11B). Thus, the deactivation hub (350) does not compress the reservoir bulb (196) and, in turn, does not inflate the tip balloon (172) such that the tip balloon (172) remains in the contracted state as shown in FIG. 11A for treating ostia and other drainage passageways of the sinuses.

In use, following insertion of the balloon dilation catheter (114) into the sinus guide catheter (312*a*), a guidewire (not shown) (e.g., Relieva Vigor® Sinus Guidewire manufactured by Acclarent Inc, Menlo Park, Calif.) or sinus illumination system (not shown) (e.g., Relieva Luma Sentry™ Sinus Illumination System shown manufactured by Acclarent Inc, Menlo Park, Calif.) is inserted through the balloon dilation catheter (114) and to the distal tip of the sinus guide catheter (312*a*). Sinus access is achieved by positioning the sinus guide catheter (312*a*) in the nasal anatomy, and advancing the guidewire (not shown) or sinus illumination system (not shown) into the cavity of the target sinus. Once sinus cavity access has been achieved, the balloon dilation catheter (114) is advanced over the sinus guidewire (not shown) or sinus illumination system (not shown) and into the target space. The dilation balloon (170) of the balloon dilation catheter (114) is then inflated to dilate the sinus ostia or other drainage passageway. Following dilation, the dilation balloon (170) is deflated. The guidewire (not shown) or sinus illumination system (not shown) is removed from the nasal anatomy followed by removal of the balloon dilation catheter (114) and the sinus guide catheter (312*a*). The balloon dilation catheter (114) can then be prepared for additional sinus dilations or Eustachian tube dilations in the same patient or other patients at that time.

It should be understood from the foregoing that instrument (110) may be readily used to dilate either the Eustachian tube (26) or various selected ostia or other drainage passageways of paranasal sinuses. If the operator wishes to dilate the Eustachian tube (26), the operator may simply couple guide catheter (112) with handle (116). Alternatively, if the operator wishes to dilate an ostium or other drainage passageway of a paranasal sinus, the operator may select the appropriate guide catheter (312*a*, 312*b*, 312*c*, 312*d*, 312*e*, 3120 from an assortment of guide catheters (312*a*, 312*b*, 312*c*, 312*d*, 312*e*, 312*f*), then couple the selected guide catheter (312*a*, 312*b*, 312*c*, 312*d*, 312*e*, 312*f*) with handle (116). If the operator intends to dilate a Eustachian tube (26) and thus chooses guide catheter (112), dilation catheter (114) will transition to a state most appropriate for dilating a Eustachian tube (26), as tip balloon (172) will inflate in response to coupling of guide catheter (112) with handle (116). With tip balloon (172) inflated, tip balloon (172) will prevent dilation catheter (114) from being advanced past the isthmus (29) into the middle ear (14). If the operator intends to dilate a sinus ostium or other sinus drainage passageway and thus chooses one of guide catheters (312a, 312b, 312c, 312d, 312e, 312f), dilation catheter (114) will remain in a state most appropriate for dilating a sinus ostium or other sinus drainage passageway, as tip balloon (172) will remain in a non-inflated state. With tip balloon (172) in a non-inflated state, dilation catheter (114) may be advanced into a sinus ostium or other sinus drainage passageway to a point where dilation balloon (170) may be successfully positioned within the sinus ostium or other sinus drainage passageway.

While the foregoing examples include an inflatable dilation balloon (170) and an inflatable tip balloon (172), it should be understood that either balloon (170, 172) or both balloons (170, 172) may be replaced with an expandable member that is operable to transition between an expanded state and a non-expanded state without requiring the movement of fluid. In other words, either balloon (170, 172) or both balloons (170, 172) may be replaced with a non-hydraulic expandable member. By way of example only, tip balloon (172) may be replaced with an elastomeric ring that is transitioned between an expanded state and a non-expanded state in response to longitudinal movement of an actuation member. For instance, if the translating actuation member is secured to the distal end of the elastomeric ring and the proximal end of the elastomeric ring is longitudinally fixed, the elastomeric ring may be expanded by driving the translating actuation member proximally; and contracted by driving the translating actuation member distally. If the translating actuation member is secured to the proximal end of the elastomeric ring and the distal end of the elastomeric ring is longitudinally fixed, the elastomeric ring may be expanded by driving the translating actuation member distally; and contracted by driving the translating actuation member proximally. Other suitable ways in which either balloon (170, 172) or both balloons (170, 172) may be replaced with a non-hydraulic expandable member will be apparent to those of ordinary skill in the art in view of the teachings herein.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A catheter system comprising: a balloon dilation catheter having a proximal end portion and a distal end portion, the balloon dilation catheter comprising: (i) an elongate shaft having a dilation balloon lumen, wherein the dilation balloon lumen is configured to couple with a first fluid supply, (ii) an expandable dilation balloon coupled to the elongate shaft and fluidly connected to the dilation balloon lumen, wherein the expandable dilation balloon is configured to transition between an inflated state and a non-inflated state, and (iii) an expandable stop element coupled to the elongate shaft, wherein the expandable stop element is distal to the expandable dilation balloon, wherein the expandable stop element is configured to transition between an expanded state and a non-expanded state, wherein the expandable dilation balloon is configured to define a larger outer diameter in the inflated state than an outer diameter defined by the expandable stop element in the expanded state.

EXAMPLE 2

The catheter system of Example 1, wherein the expandable stop element is further configured to expand radially inwardly to inhibit advancement of a guidewire through the balloon dilation catheter.

EXAMPLE 3

The catheter system of any one or more of Examples 1 through 2, wherein the expandable stop element is inflatable, wherein the elongate shaft further includes a stop element lumen.

EXAMPLE 4

The catheter of system of Example 3, wherein the stop element lumen is configured to couple with a second fluid supply.

EXAMPLE 5

The catheter system of any one or more of Examples 1 through 4, wherein the elongate shaft distally terminates at the expandable stop element such that the expandable stop element forms a distal tip of the elongate shaft.

EXAMPLE 6

The catheter system of any one or more of Examples 1 through 5, further comprising: a handle configured to be gripped by an operator, the handle comprising: (i) a guide port having a bore, wherein the bore is configured to receive a proximal end portion of the balloon dilation catheter such that the balloon dilation catheter distally projects from the handle, and (ii) a balloon catheter movement actuator configured to translate the balloon dilation catheter longitudinally relative to the handle.

EXAMPLE 7

The catheter system of Example 6, further comprising: a guide catheter received within the bore of the guide port such that the guide catheter distally projects from the handle, wherein the guide catheter is configured to slidably receive the balloon dilation catheter.

EXAMPLE 8

The catheter system of Example 7, wherein the guide catheter is configured to engage a second fluid supply assembly and thereby direct fluid into the expandable stop element lumen to thereby transition the expandable stop element to the expanded state upon insertion of the guide catheter in the bore of the guide port.

EXAMPLE 9

The catheter system of Example 8, wherein the guide catheter comprises: (i) a hub, wherein the hub has a hub body configured to be received within the bore of the guide port, wherein the hub includes a fluid source engagement feature that is configured to engage the second fluid supply and thereby direct fluid into the expandable stop element lumen to thereby transition the expandable stop element to the expanded state, and (ii) an elongate tubular shaft distally extending distally from the hub.

EXAMPLE 10

The catheter system of Example 9, wherein the fluid source engagement feature comprises a laterally projecting engagement tab, wherein the second fluid supply comprises a reservoir bulb, wherein the laterally projecting engagement tab is configured to compress the reservoir bulb from an expanded state to a compressed state and thereby drive fluid from the reservoir bulb to the expandable stop element lumen to thereby transition the expandable stop element to the expanded state in response to insertion of the hub in the bore of the guide port.

EXAMPLE 11

The catheter system of Example 10, wherein the guide port further includes a slot configured to receive the engagement tab as the hub is inserted into the guide bore.

EXAMPLE 12

The catheter system of any one or more of Examples 10 through 11, wherein the reservoir bulb is resiliently biased to assume the expanded state.

EXAMPLE 13

The catheter system of Example 7, wherein the handle further comprises a reservoir bulb in fluid communication with the expandable stop element, wherein the guide catheter is configured to not engage the reservoir bulb upon insertion of the guide catheter in the bore of the guide port.

EXAMPLE 14

The catheter system of any one or more of Examples 1 through 13, further comprising: (a) a handle configured to be gripped by an operator, the handle comprising a guide port having a bore, wherein the bore is configured to receive a proximal end portion of the balloon dilation catheter such that the balloon dilation catheter distally projects from the handle; (b) a first guide catheter, wherein the first guide catheter is configured to fit in the bore of the guide port to thereby couple with the handle, wherein the first guide catheter has a first configuration; and (c) a second guide catheter, wherein the second guide catheter is configured to fit in the bore of the guide port to thereby couple with the handle, wherein the second guide catheter has a second configuration.

EXAMPLE 15

The catheter system of any one or more of Examples 1 through 14, wherein the handle further comprises a compressible reservoir in fluid communication with the expandable stop element, wherein the first guide catheter includes a feature that is configured to compress the reservoir upon insertion of the first guide catheter in the bore to thereby drive fluid from the reservoir to the expandable stop element, wherein the second guide catheter lacks a feature that is configured to compress the reservoir upon insertion of the second guide catheter in the bore to thereby drive fluid from the reservoir to the expandable stop element.

EXAMPLE 16

The catheter system of any one or more of Examples 1 through 15, wherein the expandable stop element is resiliently biased toward the non-expanded state.

EXAMPLE 17

A dilation catheter, comprising: (a) an elongate shaft, wherein the elongate shaft defines a first lumen and a second lumen, wherein the second lumen is fluidly isolated from the first lumen; (b) an expandable dilation balloon supported by the elongate shaft, wherein the expandable dilation balloon is in fluid communication with the first lumen, wherein the expandable dilation balloon is configured to transition between an inflated state and a non-inflated state; and (c) an expandable tip balloon supported by the elongate shaft, wherein the expandable tip balloon is distal to the expandable dilation balloon, wherein the expandable tip balloon is in fluid communication with the second lumen, wherein the expandable tip balloon is configured to transition between an inflated state and a non-inflated state, wherein the expandable dilation balloon is configured to define a larger outer diameter in the inflated state than an outer diameter defined by the expandable tip balloon in the inflated state.

EXAMPLE 18

A catheter system, comprising: (a) a balloon dilation catheter comprising: (i) an expandable dilation balloon, wherein the expandable dilation balloon is configured to transition between an inflated state and a non-inflated state, and (ii) an expandable stop element, wherein the expandable stop element is distal to the expandable dilation balloon, wherein the expandable stop element is configured to transition between an expanded state and a non-expanded state; (b) a guide catheter configured to slidably receive the balloon dilation catheter, wherein the guide catheter includes a proximal hub, wherein the proximal hub comprises an actuator engagement feature; and (c) a body comprising: (i) a port configured to receive the proximal hub of the guide catheter, and (ii) an actuator in communication with the expandable stop element, wherein the actuator engagement feature is configured to engage the actuator in response to insertion of the proximal hub in the port, wherein the actuator is configured to drive the stop element to the expanded state in response to engagement of the actuator by the actuator engagement feature.

EXAMPLE 19

The catheter system of Example 18, wherein the expandable stop element comprises an inflatable member, wherein the actuator comprises a compressible fluid reservoir.

EXAMPLE 20

The catheter system of Example 19, wherein the expandable dilation balloon and the expandable stop element are fluidly isolated from each other.

VII. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A catheter system comprising:
   (a) a balloon dilation catheter having a proximal end portion and a distal end portion, the balloon dilation catheter comprising:
      (i) an elongate shaft having a dilation balloon lumen and a distal shaft end longitudinally extending to a distal tip thereof, wherein the dilation balloon lumen is configured to couple with a first fluid supply,
      (ii) an expandable dilation balloon coupled to the elongate shaft and fluidly connected to the dilation balloon lumen, wherein the expandable dilation balloon is configured to transition between an inflated state and a non-inflated state, and
      (iii) an expandable stop element coupled to the distal tip of the distal shaft end, wherein the distal shaft end of the elongate shaft extends from the expandable dilation balloon coupled thereon to the expandable stop element coupled on the distal tip such that the expandable stop element is distal to the expandable dilation balloon and longitudinally fixed relative to the expandable dilation balloon, wherein the expandable stop element is spaced apart from the expandable dilation balloon, wherein the expandable stop element is configured to transition between an expanded state and a non-expanded state,
   wherein the expandable dilation balloon is configured to define a larger outer diameter in the inflated state than an outer diameter defined by the expandable stop element in the expanded state;
   (b) a handle configured to be gripped by an operator, the handle comprising a guide port having a bore, wherein the bore is configured to receive a proximal end portion of the balloon dilation catheter such that the balloon dilation catheter distally projects from the handle, wherein the handle further comprises a compressible reservoir in fluid communication with the expandable stop element
   (c) a first guide catheter, wherein the first guide catheter is configured to fit in the bore of the guide port to thereby couple with the handle, wherein the first guide catheter has a first configuration, wherein the first guide catheter includes a feature that is configured to compress the reservoir upon insertion of the first guide catheter in the bore to thereby drive fluid from the reservoir to the expandable stop element and
   (d) a second guide catheter, wherein the second guide catheter is configured to fit in the bore of the guide port to thereby couple with the handle, wherein the second guide catheter has a second configuration.

2. The catheter system of claim 1, wherein the expandable stop element is further configured to expand radially inwardly to inhibit advancement of a guidewire through the balloon dilation catheter.

3. The catheter system of claim 1, wherein the expandable stop element is inflatable, wherein the elongate shaft further includes a stop element lumen.

4. The catheter system of claim 1, wherein the expandable dilation balloon is configured to dilate a Eustachian tube upon expansion from the non-inflated state toward the inflated state.

5. A catheter system, comprising:
(a) a balloon dilation catheter comprising:
  (i) an expandable dilation balloon, wherein the expandable dilation balloon is configured to transition between an inflated state and a non-inflated state, and
  (ii) an expandable stop element, wherein the expandable stop element is distal to the expandable dilation balloon, wherein the expandable stop element is configured to transition between an expanded state and a non-expanded state;
(b) a guide catheter configured to slidably receive the expandable dilation balloon and the expandable stop element of the balloon dilation catheter therein, wherein the guide catheter includes a proximal hub, wherein the proximal hub comprises an actuator engagement feature; and
(c) a body comprising:
  (i) a port configured to receive the proximal hub of the guide catheter, and
  (ii) an actuator in communication with the expandable stop element, wherein the actuator engagement feature is configured to engage the actuator in response to insertion of the proximal hub in the port, wherein the actuator is configured to drive the stop element to the expanded state in response to engagement of the actuator by the actuator engagement feature.

6. The catheter system of claim 5, wherein the expandable stop element comprises an inflatable member, wherein the actuator comprises a compressible fluid reservoir.

7. A catheter system comprising:
(a) a balloon dilation catheter having a proximal end portion and a distal end portion, the balloon dilation catheter comprising:
  (i) an elongate shaft having a dilation balloon lumen and a distal shaft end longitudinally extending to a distal tip thereof, wherein the dilation balloon lumen is configured to couple with a first fluid supply,
  (ii) an expandable dilation balloon coupled to the elongate shaft and fluidly connected to the dilation balloon lumen, wherein the expandable dilation balloon is configured to transition between an inflated state and a non-inflated state, and
  (iii) an expandable stop element coupled to the distal tip of the distal shaft end, wherein the distal shaft end of the elongate shaft extends from the expandable dilation balloon coupled thereon to the expandable stop element coupled on the distal tip such that the expandable stop element is distal to the expandable dilation balloon and longitudinally fixed relative to the expandable dilation balloon, wherein the expandable stop element is spaced apart from the expandable dilation balloon, wherein the expandable stop element is configured to transition between an expanded state and a non-expanded state,
  wherein the expandable dilation balloon is configured to define a larger outer diameter in the inflated state than an outer diameter defined by the expandable stop element in the expanded state;
(b) a handle configured to be gripped by an operator, the handle comprising:
  (i) a guide port having a bore, wherein the bore is configured to receive a proximal end portion of the balloon dilation catheter such that the balloon dilation catheter distally projects from the handle, and
  (ii) a balloon catheter movement actuator configured to translate the balloon dilation catheter longitudinally relative to the handle;
(c) a guide catheter received within the bore of the guide port such that the guide catheter distally projects from the handle, wherein the guide catheter is configured to slidably receive the balloon dilation catheter, wherein the guide catheter is configured to engage a second fluid supply assembly and thereby direct fluid into the expandable stop element lumen to thereby transition the expandable stop element to the expanded state upon insertion of the guide catheter in the bore of the guide port, wherein the guide catheter comprises:
  (i) a hub, wherein the hub has a hub body configured to be received within the bore of the guide port, wherein the hub includes a fluid source engagement feature that is configured to engage the second fluid supply and thereby direct fluid into the expandable stop element lumen to thereby transition the expandable stop element to the expanded state, wherein the fluid source engagement feature comprises a laterally projecting engagement tab, wherein the second fluid supply comprises a reservoir bulb, wherein the laterally projecting engagement tab is configured to compress the reservoir bulb from an expanded state to a compressed state and thereby drive fluid from the reservoir bulb to the expandable stop element lumen to thereby transition the expandable stop element to the expanded state in response to insertion of the hub in the bore of the guide port, and
  (ii) an elongate tubular shaft distally extending distally from the hub.

8. The catheter system of claim 7 wherein the guide port further includes a slot configured to receive the engagement tab as the hub is inserted into the guide bore.

9. The catheter system of claim 7 wherein the reservoir bulb is resiliently biased to assume the expanded state.

* * * * *